United States Patent
LaVoie et al.

(10) Patent No.: US 7,208,492 B2
(45) Date of Patent: Apr. 24, 2007

(54) TOPOISOMERASE-TARGETING AGENTS

(75) Inventors: Edmond J. LaVoie, Princeton Junction, NJ (US); Alexander L. Ruchelman, Robbinsville, NJ (US); Leroy F. Liu, Bridgewater, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 11/121,292

(22) Filed: May 3, 2005

(65) Prior Publication Data
US 2006/0004008 A1    Jan. 5, 2006

Related U.S. Application Data

(63) Continuation of application No. PCT/US03/36226, filed on Nov. 12, 2003.

(60) Provisional application No. 60/425,503, filed on Nov. 12, 2002, provisional application No. 60/425,535, filed on Nov. 12, 2002.

(51) Int. Cl.
*A61K 31/4355* (2006.01)
*A61K 31/5025* (2006.01)
*C07D 491/056* (2006.01)
*C07D 491/147* (2006.01)
*C07D 487/04* (2006.01)
*C07D 487/14* (2006.01)

(52) U.S. Cl. .................. 514/248; 514/280; 514/284; 514/285; 544/233; 546/48; 546/61; 546/70

(58) Field of Classification Search .......... 546/48; 514/280, 248; 544/233
See application file for complete search history.

(56) References Cited

U.S. PATENT DOCUMENTS

| | | |
|---|---|---|
| 2,915,523 A | 12/1959 | Moore et al. |
| 2,981,731 A | 4/1961 | Moore et al. |
| 2,985,661 A | 5/1961 | Hien et al. |
| 3,267,107 A | 8/1966 | Sallay |
| 3,272,707 A | 9/1966 | Tedeschi |
| 3,449,330 A | 6/1969 | Guglielmetti et al. |
| 3,538,097 A | 11/1970 | Lowe et al. |
| 3,542,782 A | 11/1970 | Houlihan et al. |
| 3,849,561 A | 11/1974 | Junzo et al. |
| 3,884,911 A | 5/1975 | Shimada et al. |
| 3,912,740 A | 10/1975 | Zee-Chang et al. |
| 4,749,708 A | 6/1988 | Maroko |
| 4,761,417 A | 8/1988 | Maroko et al. |
| 4,761,477 A | 8/1988 | Ikekawa et al. |
| 4,925,943 A | 5/1990 | Kanmacher et al. |
| 4,980,344 A | 12/1990 | Maroko |
| 5,106,863 A | 4/1992 | Hajos et al. |
| 5,126,351 A | 6/1992 | Luzzio et al. |
| 5,153,178 A | 10/1992 | Maroko |
| 5,190,753 A | 3/1993 | Behrens et al. |
| 5,244,903 A | 9/1993 | Wall et al. |
| 5,318,976 A | 6/1994 | Luzzi et al. |
| 5,639,759 A | 6/1997 | Magolda et al. |
| 5,646,283 A | 7/1997 | Suzuki et al. |

(Continued)

FOREIGN PATENT DOCUMENTS

EP    0108147 B1    5/1984

(Continued)

OTHER PUBLICATIONS

Denny, Expert Opin.Emerg.Drugs, vol. 9(1), p. 105-133 (2004).*

(Continued)

*Primary Examiner*—Emily Bernhardt
(74) *Attorney, Agent, or Firm*—Viknins Harris & Pady PLLP

(57) ABSTRACT

The invention provides compounds of formula I or formula II:

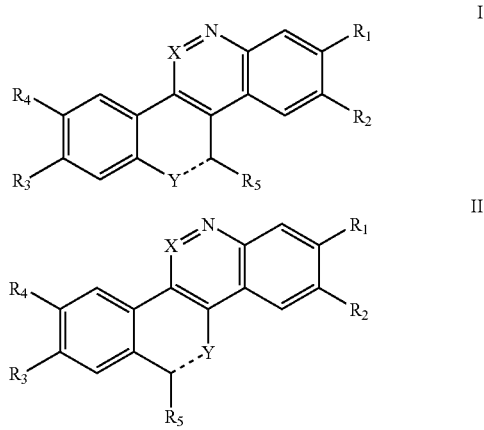

wherein:
the bond represented by --- is a single bond or a double bond, and $R_1$–$R_5$, X, and Y have any of the meanings defined in the specification and their pharmaceutically acceptable salts. The invention also provides pharmaceutical compositions comprising a compound of formula I or II, processes for preparing compounds of formula I or II, intermediates useful for preparing compounds of formula I or II, and therapeutic methods for treating cancer and other topoisomerase related conditions using compounds of formula I or II.

18 Claims, No Drawings

U.S. PATENT DOCUMENTS

| | | | |
|---|---|---|---|
| 5,767,142 | A | 6/1998 | LaVoie et al. |
| 5,770,617 | A | 6/1998 | LaVoie et al. |
| 5,807,874 | A | 9/1998 | LaVoie et al. |
| 5,981,541 | A | 11/1999 | LaVoie et al. |
| 6,140,328 | A * | 10/2000 | LaVoie et al. ............... 514/248 |
| 6,509,344 | B1 | 1/2003 | Cushman et al. |
| 6,740,650 | B2 | 5/2004 | LaVoie et al. |
| 2005/0009825 | A1 | 1/2005 | LaVoie et al. |
| 2005/0009826 | A1 | 1/2005 | LaVoie et al. |
| 2005/0010046 | A1 | 1/2005 | LaVoie et al. |

FOREIGN PATENT DOCUMENTS

| | | | |
|---|---|---|---|
| EP | 0496634 | A1 | 7/1992 |
| GB | 2108955 | A | 5/1983 |
| SU | 1530628 | | 12/1989 |
| WO | WO-92/21661 | A1 | 12/1992 |
| WO | WO-96/36612 | A1 | 11/1996 |
| WO | WO-97/29106 | A1 | 8/1997 |
| WO | WO-98/12181 | A1 | 3/1998 |
| WO | WO-98/31673 | A1 | 7/1998 |
| WO | WO-99/31067 | A1 | 6/1999 |
| WO | WO-00/21537 | A1 | 4/2000 |
| WO | WO-01/32631 | A2 | 5/2001 |
| WO | 03/047505 | * | 11/2002 |
| WO | WO-03/041660 | A2 | 5/2003 |
| WO | WO-03/047505 | A2 | 6/2003 |
| WO | WO-2004/014918 | A1 | 2/2004 |

OTHER PUBLICATIONS

Ruchelman et al. Bioorganic & Medicinal Chemistry Letters, vol. 14, p. 5585-5589 (2004).*

Aguirre, J. M., et al., "Reaction of 1,2-diarylethylamides with ethyl polyphosphate(EPP): correlation of the von Braun, Ritter and Bischler-Napieralski reactions." *Chemical Abstracts*, 111(13), Abstract No. 115004, (1989), 646.

Akiyama, Shin-Ichi, et al., "Isolation and Genetic Characterization of Human KB Cell Lines Resistant to Multiple Drugs", *Somatic Cell and Molecular Genetics*, 11(2), (1985), 117-126.

Andoh, Toshiwo, et al., "Characterization of a mammalian mutant with a camptothecin-resistant DNA topoisomerase I", *Proceedings of the National Academy of Sciences USA*, 84(16), (1987), 5565-5569.

Andoh, Toshiwo, et al., "Drug resistance mechanisms of topoisomeras I drugs", *Advances in Pharmacology, vol. 29B, DNA Topoisomerases: Topoisomerase- Targeting Drugs*, (1994), 93-103.

Arumugam, N., et al., "Synthesis of 7,8-Benzophenanthridines", *Indian Journal of Chemistry*, vol. 12, (1974), 664-667.

Badia, Dolores, et al., "Silicon-mediated isoquinoline synthesis: preparation and stereochemical characterization of 4-hydroxy-3-phenylisoquinolines", *Chemical Abstracts*, 117(13), Abstract No. 131034, (1992), 730.

Baezner, C., et al., "Uberfuhrung von o-nitro- und o,dinitrobenzylchlorid in acridinderivate", *Berichte der Deutschen Chemischen Gesellschaft*, 39, English Title—Conversion of o-nitro and o,p-dinitrobenzylchlroide into acridinic derivatives, (1906), 2438-2447.

Baezner, Carlo, "Uberfuhrung von o-nitro-und o, p-dinitrobenzylchlorid in acridinderivate", *Berichte der Deutschen Chemischen Gesellschaft*, 37, English Title—Conversion of o-nitrobenzyl chloride and o,p-dinitrobenzyl chloride into acridine derivatives, (1904), 3077-3083.

Bhakuni, D. S., et al., "Protoberberine Alkaloids", *The Alkaloids*, vol. 28, Chapter 2, Academic Press, Inc., (1986), 95-181.

Bjornsit, Mary-Ann, et al., "Expression of human DNA topoisomerase I in yeast cells lacking yeast DNA topoisomerase I: restoration of sensitivity of the cells to the antitumor drug camptothecin", *Cancer Research*, 49, (1989), 6318-6323.

Bradsher, Charles K., et al., "alpha-Acyl-o-toluitriles as intermediates in the preparation of 3-substituted isoquinolines and 1-amino-2-benzopyrylium derivatives", *Chemical Abstracts*, 89(21), Abstract No. 89: 179810b,(1978), 590.

Brossi, Arnold, "Benzo[c]phenanthridine Alkaloids", *The Alkaloids, Chemistry and Pharmacology*, vol XXV, Academic Press, Inc., (1985), 178-199.

Buu-Hoi, N. P., et al., "Carcinogenic Nitrogen Compounds. XV. Polysubstituted Angular Benacridines and Benzophenarsazines", *Chemical Abstracts*, 49(1), Abstract, col. 330, 10-Organic Chemistry, (1955), 329-330.

Buu-Hoi, N. G., et al., "The Chemistry of Carcinogenic Nitrogen Compounds. Part X. The Pfitzinger Reaction in the Synthesis of 1:2-Benzacridines", *Journal of the Chemical Society*, Letchworth, GB, (1952), 279-281.

Buu-Hoi, N. G., "The chemistry of carcinogenic nitrogen compounds. Part V. Angular hydroxybenzacridines and hydroxdibenzacridines", *Journal of the Chemical Society*, Letchworth GB, (1950), 2096-2099.

Carmichael, James, "Evaluation of a tetrazolium-based semiautomated colorimetric assay: assessment of chemosensitivity testing", *Cancer Research*, 47, (1987), 936-42.

Chen, Allan Y., "A new mammalian DNA topoisomerase I posion Hoechst 33342: cytotoxicity and drug resistance in human cell cultures", *Cancer Research*, 53(6), (1993), 1332-1337.

Chen, Allan Y., et al., "DNA Minor Groove-Binding Ligands: A Different Class of Mammalian DNA Topoisomerase I Inhibitors", *Proceedings of the National Academy of Sciences of the United States of America*, 90, (1993), 8131-8135.

Chen, Allan Y., et al., "DNA Topoisomerases: Essential Enzymes and Lethal Targets", *Annu. Rev. Pharmacol. Toxicol.*, 34, (1994), 191-218.

Cherif, Abdallah, et al., "N-(5,5-Diacetoxypent-1-yl)doxorubicin: a new intensely potent doxorubicin analogue", *Journal of Medicinal Chemistry*, 35, (Aug. 21, 1992), 3208-3214.

Croisy-Delcey, M., et al., "Synthesis and Carcinogenic Activity of Oxidized Benzacridines: Potential Metabolites of the Strong Carcinogen 7-methylbenz[c]acridine and of the Inactive Isomer 12-methylbenz[a]acridine", *Chemical Abstracts*, 98, Abstract No. 43798, (1983), 27-29.

Croisy-Delcey, M., et al., "Synthesis and carcinogenic activity of oxidized benzacridines: potential metabolites of the strong carcinogenic 7-methylbenz[c]acridine and of the inactive isomer 12-methylbenz[a]acridine." *Journal of Medicinal Chemistry*, 26, (1983), 303-306 (Abstract).

Cushman, Mark, et al., "Synthesis and antitumor activity of structural analogues of the anticancer benzophenanthridine alkaloid fagaronine chloride", *Journal of Medicinal Chemistry*, 28, (1985), 1031-1036.

Cushman, Mark, et al., "Synthesis of New Indeno[1,2-c]isoquinolines: Cytotoxic Non-Camptothecin Topoisomerase I Inhibitors", *Journal of Medicinal Chemistry*, 43(20), (2000), 3688-3698.

D'Arpa, Peter, et al., "Topoisomerase-targeting antitumor drugs", *Biochimica et Biophysica Acta*, 989, (1989),163-177.

Denizot, F., et al., "Rapid colorimetric assay for cell growth and survival. Modifications to the tetrazolium dye procedure giving improved sensitivity and reliability", *Journal of Immunological Methods*, 89, (1986), 271-277.

Dominguez, Esther, et al., "Dehydrogenation reactions of 1-substituted-3-aryltetrahydroisoquinoline derivatives", *Chemical Abstracts*, 101(11), Abstract No. 090742z,(1984),624.

Dorofeenko, G. N., et al., "Synthesis of 3-aryl derivatives of 2-benzopyrylium salts with free alpha-positions", *Chemical Abstracts*, 74 (15), Abstract No. 076295, (1971), 432.

Fitzgerald, J. J., et al., "Reaction of benzocyclobutene oxides with nitriles: synthesis of hypecumine and other 3-substituted isoquinolines", *Chemical Abstracts*, 122(7), Abstract No. 081704, (1995), 1128.

Fox, G. J., et al., "para-Bromination of Aromatic Amines: 4-Bromo-N,N-Dimethyl-3-(Trifluoromethyl)Aniline", *Organic Syntheses*, vol. 55, (1976), 20-23.

Fujii, Noboru, et al., "Induction of Mammalian DNA Topoisomerase I-mediated DNA Cleavabe and DNA Winding by Bulgarein", *Journal of Biological Chemistry,* 268(18), (1993), 13160-13165.

Gallo, Robert C., et al., "Studies on the Antitumor Activity, Mechanism of Action, and Cell Cycle Effects of Camptothecin", *Journal of the National Cancer Institute*, vol. 46, No. 4, (1971), pp. 789-795.

Garcia, Alberto, et al., "A simple direct approach to 1-substituted 3-arylisoquinolines from deoxybenzoins and ntriles", *Chemical Abstracts*, 110(25), Abstract No. 23107u, (1989), 622.

Gatto, Barbara, "Identification of Topoisomerase I as the Cyctotoxic Target of the Protoberberine Alkaloid Coralyne", *Cancer Research,* 56(12), (1996),2795-2800.

Giovanella, Beppino C., et al., "Complete growth inhibition of human cancer xenografts in nude mice by treatment with 20-(S)-camptothecin", *Cancer Research,* 51(11), (1991), 3052-3055.

Godowski, K. C., et al., "Free amine benzophenanthridine alkaloid compositions", *USPATFULL Database*, No. 95:20510, RN No. 218-38-2 (Benzo[c]phenanthradine), from U.S. Patent 5,395,615, (1995), 3 pages.

Goldman, Gustavo H., et al., "Differential poisoning of human and *Aspergillus nidulans* DNA topoisomerase I by bi- and terbenzimidazoles", *Biochemistry,* 36(21), (1997), 6488-6494.

Gopinath, K. W., et al., "Synthesis of Some 1:2- and 7:8- Benzophenanthridine", *Journal of the Chemistry Society,* 78(2), (1958), 504-509.

Hahn, F. E., et al., "Berberine", *In: Antibiotics, Mechanism of Action of Antimicrobial and Antitumor Agents, vol. III,* J.W. Corcoran, et al., (eds.), Springer-Verlag, (1975), 577-584.

Halligan, Brian D., et al., "Purification and Characterization of a Type II DNA Topoisomerase from Bovine Calf Thymus", *The Journal of Biological Chemistry,* 260(4), (1985), 2475-2482.

Hoan, Nguyen, et al., "Syntheses from o-halogenated anisoles and phenetoles", *Chemical Abstracts*, 41(20), American Chemical Society, Abstract No. 6571bg, (1947), 2 pages.

Hsiang, Yaw-Huei, et al., "Identification of Mammalian DNA Topoisomerase I as an Intracellular Target of the Anticancer Drug Camptothecin", *Cancer Research,* 48(7), (1988), 1722-1726.

Iwao, Masatomo, et al., "A Regiospecific Synthesis of Carbazoles via Consecutive Palladium-Catalyzed Cross-coupling and Aryne-Mediated Cyclization", *Heterocycles,* 36, (1993), 1483-1488.

Izmail'skii, V. A., et al., "Absorption Spectra of Molecular Complexes of Derivatives of Benzacridine and Dibenzacridine", *Chemical Abstracts*, 54(8), Abstract, col. 7335b, (1960), 3 pages.

Jacob, Juergen, et al., "Monooxygenase Induction by Various Xenobiotics and its Influence on Rat Liver Microsomal Metabolism by Chrysene in Comparison to Benz[a]anthracene", *Chemical Abstracts,* 107, Abstract No. 34760, (1987), 2 p.

Janin, Yves L., et al., "Synthesis and Evaluation of New 6-Amino-Substituted Benzo[c]phenanthridine Derivatives", *Journal of Medicinal Chemistry,* 36(23), (1993), 3686-3692.

Jayaraman, M., et al., "Synthesis of New Dihydroindeno [1,2-c] isoquinoline and Indenoisoquinolinium Chloride Topoisomerase Inhibitors Having High in Vivo Anticancer Activity in the Hollow Fiber Animal Model", *Journal of Medicinal Chemistry,* 45(1), (2002), 242-249.

Kametani, Tetsuji, et al., "Studies on the synthesis of heterocyclic compounds. DCXXVII. The formation of 2,3,9,10-tetramethoxybenz[c]acridine by treatment of 6,7-dimethoxy-1-(4,5-dimethoxy-2-nitrophenethyl)-2-methylisoquinoline with triethyl phosphite", *Chemical and Pharmaceutical Bulletin,* 23(9), (1975), 2025-2028.

Kametani, T., et al., "Synthesis of Heterocyclic Compounds. DCXXVII. Formation of 2,3,9,10-tetramethoxybenz[c]acridine by treatment of 6,7-dimethoxy-1-(4,5-dimethoxy-2-nitrophenethyl)-2-methylisoquinoline with Triethyl Phosphite", *Chemical Abstracts,* 84, Abstract No. 43798, (1976), 1 p.

Kanmacher, I., et al., "Synthesis of Isoquino[1,2-b]quinazolines by Cycloaddition Reaction", *Chemical Abstracts,* 114, Abstract No. 207191, (1990), 4 pages.

Kar, G. K., et al., "Regioselective Thermal Cyclization of 3-substituted Arylenaminoimine hydrochlorides. A convenient method for the synthesis of Functionalized Polycyclic Quinoline Derivatives", *Chemical Abstracts,* 123, Abstract No. 11828,(1995), 1 p.

Kerrigan, J. E., et al., "5H-8,9-Dimethoxy-5-(2-N,N-dimethylaminoethyl)dibenzo[c, h][1,6]naphthyridin-6-ones and Related Compounds as TOP1-Targeting Agents: Influence of Structure on the Ternary Cleavable Complex Formation", *Bioorganic and Medicinal Chemistry Letters,* 13, (2003), 3395-3399.

Kessar, S V., et al., "Azasteroids. Part VII. Synthesis of 7-hydroxy-2-methoxy-7,8,9,10-tetrahydrobenzo[i]phenanthridine", *J. Chem. Soc.,* (1971), 259-261.

Kessar, S. V., et al., "New Routes to Condensed Polynuclear Compounds: Part X-Synthesis of Some Benzo[i]phenanthridine through Benzyne Cyclization", *Indian Journal of Chemistry,* 11, (1973), pp. 624-627.

Kim, J. S., et al., "Influence of steric factors on topoisomerase I inhibition and cytotoxicity of bisbenzimidazoles related to Hoechst 33342", *Proceedings of the 86th Annual Meeting of the American Association for Cancer Research,* 36, Abstract No. 2689, Toronto, Ontario, Canada,(Mar. 1995),p. 451.

Kim, J. S., et al., "Influence of steric factors on topoisomerase I inhibition and cytotoxicity of bisbenzimidazoles related to Hoechst 33342", *Abstract 7—Proceedings of the 3rd Annual Scientific Retreat of the Cancer Institute of New Jersey,* Princeton Marriott Forrestal Village, (1995), p. 28.

Kim, Jung S., et al., "Quantitative structure-activity relationships on 5-substituted terbenzimidazoles as topoisomerase I poisons and antitumor agents", *Bioorganic & Medicinal Chemistry,* 6(2), (1998), 4 pages (Abstract).

Kim, J. S., et al., "Steric factors associated with the topoisomerase I inhibition and cytotoxicity of substituted bisbenzimidazoles", *Abstract 10- Proceedings of the American Association of Pharmaceutical Scientists Eastern Regional Meeting,* (1995), p. 27.

Kim, Jung S., et al., "Structure-activity Relationships of Benzimidazoles and Related Heterocycles as Topoisomerase I Poisons", *Bioorganic & Med. Chem.,* 4, (1996), pp. 621-630.

Kim, Jung S., "Substituted 2,5'-Bi-1H-benzimidazoles: Topoisomerase I Inhibition and Cytotoxicity", *Journal of Medicinal Chemistry,* 39(4), (1996), 992-998.

Kim, Jung, S., et al., "Terbenzimidazoles: influence of 2"-, 4-, and 5-subtituents on cytotoxicity and relative potency as topoisomerase I poisons", *Journal of Medicinal Chemistry,* 40(18), (1997), 2818-2824.

Kitamura, Tsugio , et al., "Isoquinoline derivatives from the Ritter-type reaction of vinyl cations", *Chemical Abstracts,* 102(1), Abstract No. 6157c, (1985).

Klopman, Gilles , et al., "Testing by Artificial Intelligence: Computational Alternatives to the Determination of Mutagenicity", *Chemical Abstracts,* 118, Abstract No. 17489, (1993), 1 p.

Knab, A. M., et al., "Mechanisms of Camptothecin Resistance in Yeast DNA Topoisomerase I Mutants", *Journal of Biological Chemistry,* 268(30), (1993), 22322-22330.

Lavoie, E. J., et al., "Structure-activity studies related to minor groove-binding ligands which inhibit mammalian DNA topoisomerase I", *Abstract 1—Proceedings of the 85th Annual Meeting of American Association for Cancer Research,* San Francisco, CA, (Apr. 1994), p. 2699.

Lee, Jeremy S., et al., "Coralyne binds tightly to both T A T- and C G C+-containing DNA triplexes", *Biochemistry,* 32(21), (1993), 5591-5597.

Liu, Leroy F., et al., "Cleavage of DNA by Mammalian DNA Topoisomerase II", *Journal of Biological Chemistry,* vol. 258, No. 24, (1983), 15365-15370.

Makhey, Darshan, "Coralyne and Related Compounds as Mammalian Topoisomerase I and Topoisomerase II Poisons", *Bioorganic & Medicinal Chemistry,* 4(6), (1996), 781-791.

Makhey, Darshan, "Protoberberine Alkaloids and Related Compounds as Dual Inhibitors of Mammalian Topoisomerase I and II", *Medicinal Chemistry Research,* 5(1), (1994), 1-12.

Meegalla, Sanath K., et al., "Synthesis and Pharmacological Evaluation of Isoindolo[1,2-b]quinazolinone and Isoindolo[2,1-a]benzimidazole Derivatives Related to the Antitumor Agent Batracylin", *J. Med. Chem.,* 37, (1994), pp. 3434-3439.

Memetzidis, G., et al., "Structure-affinity relationships of berbines or 5,6,13, 13a-tetrahydro-8H-dibenzo[a,g]quinolizines at alpha-adrenoceptors", *European Journal of Medicinal Chemistry,* 26, (1991), 605-611.

Messmer, F. M., et al., "Fagaronine, a New Tumor Inhibitor Isolated from *Fagara zanthoxyloides* Lam. (Rutaceae)", *Journal of Pharmaceutical Sciences,* (1972), 1858-1859.

Mohanty, N. , et al., "New Therapeutic agents of the quinoline series. I. Fused quinolyl compounds", *Chemical Abstracts,* (1968), p. 1792.

Mosmann, Tim , "Rapid Colorimetric Assay for Cellular Growth and Survival: Application to Proliferation and Cytotoxicity Assays", *Journal of Immunological Methods,* 65(1-2), (1983), 55-63.

Nelson, Janis T., et al., "Proton and carbon-13 NMR spectra of fifteen substituted isoquinolines", *Chemical Abstract,* 115(5), Abstract No. 048721, (1991), 753.

Peters, Dan , et al., "Synthesis of Various 5-Substituted Uracils", *Journal of Heterocyclic Chemistry,* 27, (Nov.-Dec. 1990), 2165-2173.

Pilch, Daniel S., et al., "A terbenzimidazole that preferentially binds and conformationally alters structurally distinct DNA duplex domains: a potential mechanism for topoisomerase I poisoning", *Proc. Nat'l. Acad. Sci. USA,* 94(25), (1997), 13565-13570.

Pilch, Daniel S., et al., "Biophysical Characterization of a Cytotoxic, Topoisomerase I Poison", *Abstract 8—Proceedings of the 3rd Annual Scientific Retreat of the Cancer Institute of New Jersey,* Princeton Marriott Forrestal Village, Princeton, NJ, (Jun. 1, 1995), 2 Pages.

Pilch, Daniel S., et al., "Characterizing the DNA binding modes of a topoisomerase I-poisoning terbenzimidazole: evidence for both intercalative and minor groove binding properties", *Drug Design and Discovery,* 13, (1996), 115-133.

Piper, J. R., et al., "Synthesis and Antifolate Activity of 5-Methyl-5,10-dideaza Analogues of Aminopterin and Folic Acid and an Alternative Synthesis of 5, 10-Dideazatetrahydrofolic Acid, a Potent Inhibitor of Glycinamide Ribonucleotide Formyltransferase", *J. Med. Chem.,* 31, (1988), pp. 2164-2169.

Porai-Koshits, B. A., et al., "Imidazole derivatives. IV. Synthesis of some polybenzimidazoles", *J. Gen. Chem. USSR,* 23, As related in Chemical Abstracts, 48(10) (1954), Col. 12740, (1953), pp. 873-879.

Quast, Ulrich , et al., "Heterocyclic alpha-carbinolamines with the isoquinuclidines skeleton. 3. Benzoisoquinuclidines", *Chemical Abstracts,* 97 (21), Abstract No. 182180s, (1982), 806.

Ramesh, D., et al., "Studies on Polycyclic Azaarenes. 2. Sythesis of Trans-3,4-dihydroxy-3,-dihydrobenz[c]acridine and trans-8,9-dihydroxy-8,9-dihydrobenz[c]acridine", *Chemical Abstracts,* 108, Abstract No. 37626, (1988), 2 pgs.

Ray, Jayanta K., et al., "A Facile and Convenient Method for the Synthesis of 8-methoxy-10,11-dihydronaphtho[1,2-b]quinolines", *Chemical Abstracts,* 92, Abstract No. 76254, (1980), 30-31.

Safaryan, G. P., et al. "2-Benzopyrylium salts. 25, Reaction of 2-benzopyrylium salts with some nucleophiles", *Chemical Abstracts,* 96(17), Abstract No. 142656z, (1982), 739.

Schiess, P., et al., "Thermolytic ring opening of acyloxybenzocyclobutenes: an efficient route to 3-substituted isoquinolines", *Chemical Abstracts,* 104(19), Abstract No. 168332z, (1986), 639.

Sethi, Manohar L., "Enzyme Inhibition VI: Inhibition of Reverse Transcriptase Activity by Protoberberine Alkaloids and Structure-Activity Relationships", *Journal of Pharmaceutical Sciences,* 72(5), (1983), 538-541.

Shcherbakova, I. V., et al., "2-Benzopyrilium salts. 35. Synthesis of the natural alkaloid dehydronocoralydine and other substituted salts of dibenzo[a,g] quinolizine", *Chemical Abstracts,* 112 (19), Abstract No. 179554, (1990), 823.

Singh, S. K., et al., "Nitro and Amino Substitution in the D-Ring of 5-(2-Dimethylaminoethyl)-2,3-methylenedioxy-5H-dibenzo [c,h][1,6] naphthyridin-6-ones: Effect on Topoisomerase-I Targeting Activity and Cytotoxicity", *Journal of Medicinal Chemistry,*46(11), (2003), 2254-2257.

Singh, Malvinder P., et al., "Synthesis and Sequence-Specific DNA Binding of a Topoisomerase Inhibitory Analog of Hoechst 33258 Designed for Altered Base and Sequence Recognition", *Chem. Res. Toxicol.,* 5, (1992), pp. 597-607.

Sotomayor, N. , et al., "Oxidation reactions of 2'-functionalized 3-aryltetrahydro-and 3,4-dihydroisoquinolines", *Chemical Abstracts,* 124 (11), Abstract No. 145854, (1996), p. 1227.

Southard, G. L., et al., "Drug Delivery Devices", *USPATFULL Database,* No. 91:36238, RN No. 218-38-2 (Benzo[c]phenanthradine), from U.S. Patent 5,013,553, (1991), 2 pages.

Stermitz, Frank R., "Synthesis and Biological Activity of Some Antitumor Benzophenanthridinum Salts", *Journal of Medicinal Chemistry,* 18(7), (1975),708-713.

Studier, F. W., et al., "Use of T7 RNA polymerase to direct expression of cloned genes", *Methods in Enzymology,* 185, (1990), 60-89.

Sun, Qun, et al., "Structure activity of novel topoisomerase I inhibitors related to Hoechst 33342", *Abstract 6—Proceedings of the American Association of Pharmaceutical Scientists Eastern Regional Meeting,* Hyatt Regency Hotel, New Brunswick, NJ, (Jun. 5-6, 1995), p. 25.

Sun, Qun, et al., "Structure Activity of Topoisomerase I Poisons Related to Hoechst 33342", *Bioorganic & Medicinal Chemistry Letters,* 4 (24), (1994), pp. 2871-2876.

Sun, Qun, et al., "Structure-activity studies related to minor groove-binding ligands which inhibit mammalian DNA topoisomerase I", *Cancer Institute of New Jersey's First Annual Scientific Retreat, Abstract 2,* Princeton Marriott Forrestal Village, Princeton, NJ, (Jun. 7, 1994), p. 66.

Sun, Q., et al., "Synthesis and evaluation of terbenzimidazoles as topoisomerase I inhibitors", *Journal of Medicinal Chemistry,* 38(18), (1995), 3638-3644.

Sun, Qun , et al., "Synthesis and Evaluation of Terbenzimidazoles as Topoisomerase I Inhibitors", *Chemical Abstracts,* vol. 123, No. 15, Abstract No. 198740r, (1995), 1241.

Sun, Qun, et al., "Synthesis and Pharmacological Evaluation of a Series of Novel DNA Topoisomerase I Inhibitors as Antitumor Agents", *Scientific Proceedings of 86th Annual Meeting of the American Association for Cancer Research,* Abstract 3, vol. 36, Toronto, Canada, (Mar. 1995).

Sun, Qun, et al., "Synthesis and pharmacological evaluation of a series of novel DNA topoisomerase I inhibitors as antitumor agents", *Abstract 5—Proceedings of the 3rd Annual Scientific Retreat of the Cancer Institute of New Jersey,* Princeton Marriott Forrestal Village, Princeton, NJ, (1995), p. 27.

Sun, Qun , et al., "Synthesis of Benzimidazo[2,1-a]isoquinolines", *Syn. Lett., submitted,* Paper No. 7,(1995), 6 pages.

Tamura, H. , et al., "Molecular cloning of a cDNA of a camptothecin-resistant human DNA topoisomerase I and identification of mutation sites", *Nucleic Acids Research,* 19 (1), (1991), pp. 69-75.

Tewey, K M., et al., "Adriamycin-induced DNA damage mediated by mammalian DNA topoisomerase II", *Science,* 226(4673), (1984), 466-8.

Vinogradov, A. E., et al., "Some properties of new DNA specific bisbenzimidazole fluorochromes without a piperazine ring", *Biotechnic & Histochemistry,* 68 (5), (1993), pp. 265-270.

Walterova, D., et al., "Isolation, Chemistry and Biology of Alkaloids from plants of Papaveraceae. Part XCV. Practical application of isotachophoresis in analysis of isoquinoline alkaloids", *Chemical Abstract,* vol. 104, No. 12, (1986), No. 95573.

Wang, Li-Kai, et al., "Inhibition of Topoisomerase I Function by Coralyne and 5,6 -Dihydrocoralyne", *Chem. Res. Toxicol.,* 9, (1996), pp. 75-83.

Wang, Li-Kai, et al., "Inhibition of Topoisomerase I Function by Nitidine and Fagaronine", *Chem. Res. Toxicol.,* 6, (1993), pp. 813-818.

Wang, Huimin, et al., "Stimulation of topoisomerase II-mediated DNA damage via a mechanism involving protein thiolation", *Biochemistry,* 40(11), American Chemical Society,(2001),3316-3323.

Waters, W. A., et al., "Reactions of Free Benzyl Radicals with Benz[a]- and Benz[c]acridine", *Chemical Abstracts*, 54 (4), Abstract, col. 3424b, (1960).

Wilson, W. D., et al., "Coralyne. Intercalation with DNA as a Possible Mechanism of Antileukemic Action", *Journal of Medicinal Chemistry*, 19(10), Communications to the Editor, (1976), 1261-1263.

Yadagiri, Bathini, et al., "Convenient Routes to Substituted Benzimidazoles and Imidazolo[4,5-b]pyridines Using Nitrobenzene as Oxidant", *Synthetic Communications*, 20 (7), (1990), 955-963.

Yamamoto, Yutaka, et al., "Reaction of 6H-1, 3-oxazin-6-one with benzyne giving isoquinoline derivatives", *Chemical Abstracts*, 118(7), Abstract No. 059563u, (1993), 831.

Yamashita, Yoshinori, et al., "Induction of Mammalian DNA Topoisomerase I and II Mediated DNA Cleavage by Saintopin, a New Antitumor Agent from Fungus", *Biochemistry*, 30(24), (1991), 5838-5845.

Yamashita, Yoshinori, "Induction of Mammalian DNA Topoisomerase I Mediated DNA Cleavage by Antitumor Indolocarbazole Derivatives", *Biochemistry*, 31(48), (1992), 12069-12075.

Zee-Cheng, K., et al., "Experimental Antileukemic Agents. Coralyne, Analogs, and Related Compounds", *Journal of Medicinal Chemistry*, 17(3), (1974), 347-351.

Zee-Cheng, K. Y., et al., "Practical Preparation of Coralyne Chloride", *Journal of Pharmaceutical Sciences*, 61 (6), (1972), 969-971.

Zee-Cheng, R. K., et al., "Tetramethoxydibenzoquinolizinium Salts. Preparation and Antileukemic Activity of Some Positional and Structural Isomers of Coralyne", *Journal of Medicinal Chemistry*, 19(7), (1976), 882-886.

\* cited by examiner

TOPOISOMERASE-TARGETING AGENTS

CROSS-REFERENCE TO RELATED APPLICATIONS

This application is a continuation of international application number PCT/US03/36226, filed 12 Nov. 2003; which application also claims priority to U.S. Provisional Application No. 60/425,503, filed on 12 Nov. 2002 and to U.S. Provisional Application No. 60/425,535 filed on 12 Nov. 2002, the specifications of which are herein incorporated by reference.

BACKGROUND OF THE INVENTION

DNA-topoisomerases are enzymes which are present in the nuclei of cells where they catalyze the breaking and rejoining of DNA strands, which control the topological state of DNA. Recent studies also suggest that topoisomerases are also involved in regulating template supercoiling during RNA transcription. There are two major classes of mammalian topoisomerases. DNA-topoisomerase-I catalyzes changes in the topological state of duplex DNA by performing transient single-strand breakage-union cycles. In contrast, mammalian topoisomerase II alters the topology of DNA by causing a transient enzyme bridged double-strand break, followed by strand passing and resealing. Mammalian topoisomerase II has been further classified as Type II α and Type II β. The antitumor activity associated with agents that are topoisomerase poisons is associated with their ability to stabilize the enzyme-DNA cleavable complex. This drug-induced stabilization of the enzyme-DNA cleavable complex effectively converts the enzyme into a cellular poison.

Several antitumor agents in clinical use have potent activity as mammalian topoisomerase II poisons. These include adriamycin, actinomycin D, daunomycin, VP-16, and VM-26 (teniposide or epipodophyllotoxin). In contrast to the number of clinical and experimental drugs which act as topoisomerase II poisons, there are currently only a limited number of agents which have been identified as topoisomerase I poisons. Camptothecin and its structurally-related analogs are among the most extensively studied topoisomerase I poisons. Recently, bi- and terbenzimidazoles (Chen et al., *Cancer Res.* 1993, 53, 1332–1335; Sun et al., *J. Med. Chem.* 1995, 38, 3638–3644; Kim et al., *J. Med. Chem.* 1996, 39, 992–998), certain benzo[c]phenanthridine and protoberberine alkaloids and their synthetic analogs (Makhey et al., *Med. Chem. Res.* 1995, 5, 1–12; Janin et al., *J. Med. Chem.* 1975, 18, 708–713; Makhey et al., *Bioorg. & Med. Chem.* 1996, 4, 781–791), as well as the fungal metabolites, bulgarein (Fujii et al., *J. Biol. Chem.* 1993, 268, 13160–13165) and saintopin (Yamashita et al., *Biochemistry* 1991, 30, 5838–5845) and indolocarbazoles (Yamashita et al., *Biochemistry* 1992, 31, 12069–12075) have been identified as topoisomerase I poisons. Other topoisomerase poisons have been identified including certain benzo[i]phenanthridine and cinnoline compounds (see LaVoie et al., U.S. Pat. No. 6,140,328 and WO 01/32631). Despite these reports there is currently a need for additional agents that are useful for treating cancer.

SUMMARY OF THE INVENTION

Applicant has discovered compounds that show inhibitory activity against topoisomerase I and/or topoisomerase II, and compounds that are effective cytotoxic agents against cancer cells, including drug-resistant cancer cells. Accordingly, the invention provides a compound of the invention which is a compound of formula I or formula II:

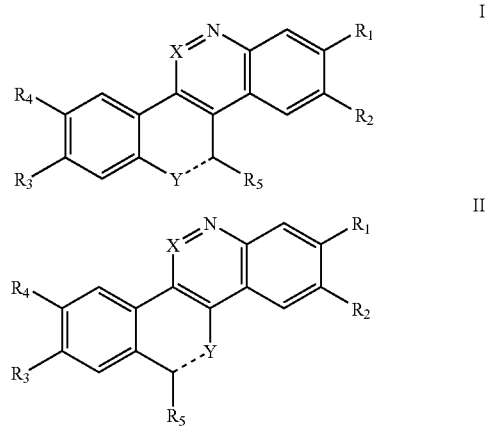

wherein:
the bond represented by --- is a single bond or a double bond;
X is CH or N;
Y is CH or N when the bond represented --- is a double bond, or Y is $CH_2$ or $NR_x$ when the bond represented --- is a single bond;
one of $R_1$ and $R_2$ is nitro, halo, or $(C_1-C_6)$alkoxy and the other is hydrogen, nitro, halo, or $(C_1-C_6)$alkoxy; or $R_1$ and $R_2$ taken together are methylenedioxy;
one of $R_3$ and $R_4$ is nitro, halo, or $(C_1-C_6)$alkoxy and the other of $R_3$ and $R_4$ is hydrogen, nitro, halo, or $(C_1-C_6)$alkoxy; or $R_3$ and $R_4$ taken together are methylenedioxy;
$R_5$ is a solubilizing group; and
$R_x$ is hydrogen or $(C_1-C_6)$alkyl;
or a pharmaceutically acceptable salt thereof. Preferably, Y is not N, when $R_5$ is —OH.

The invention also provides a pharmaceutical composition comprising a effective amount of a compound of the invention in combination with a pharmaceutically acceptable diluent or carrier.

The invention also provides a method of inhibiting cancer cell growth, comprising administering to a mammal afflicted with cancer, an amount of a compound of the invention, effective to inhibit the growth of said cancer cells.

The invention also provides a method comprising inhibiting cancer cell growth by contacting said cancer cell in vitro or in vivo with an amount of a compound of the invention, effective to inhibit the growth of said cancer cell.

The invention also provides a method for modulating topoisomerase activity in a mammal in need of such treatment comprising administering to the mammal, an amount of a compound of the invention effective to provide a topoisomerase modulating effect.

The invention also provides a compound of the invention for use in medical therapy, preferably for use in treating cancer, for example, solid tumors, as well as the use of a compound of the invention for the manufacture of a medicament useful for the treatment of cancer, for example, solid tumors.

The invention also provides the use of a compound of the invention for the manufacture of a medicament useful for modulating the activity of a topoisomerase.

The invention also provides processes and novel intermediates disclosed herein (e.g. in the Schemes hereinbelow) which are useful for preparing compounds of the invention. Some of the compounds of formula I and II are useful to prepare other compounds of formula I and II.

DETAILED DESCRIPTION

The following definitions are used, unless otherwise described.

"$(C_1–C_6)$alkyl" denotes a straight or branched carbon chain with 1, 2, 3, 4, 5, or 6, carbon atoms, but reference to an individual radical such as "propyl" embraces only the straight chain radical, a branched chain isomer such as "isopropyl" being specifically referred to.

"$(C_3–C_6)$cycloalkyl" denotes a carbocyclic ring with 3, 4, 5, or 6, carbon atoms.

"Aryl" denotes a phenyl radical or an ortho-fused bicyclic carbocyclic radical having about nine to ten ring atoms in which at least one ring is aromatic. Examples of aryl include phenyl, indenyl, and naphthyl.

"Aryl$(C_1–C_6)$alkyl" refers to a group of the formula aryl-$(C_1–C_6)$alkyl-, where aryl and $(C_1–C_6)$alkyl are as defined herein.

"Halo" is fluoro, chloro, bromo, or iodo.

"Solubilizing group" is a substituent that increases the water solubility of the compound of formula I or II compared to the corresponding compound lacking the substituent (i.e. wherein the substituent is hydrogen). Examples of solubilizing groups include $(C_1–C_6)$ alkoxycarbonyl (e.g. —$CO_2Me$), cyano, halo, hydroxy, mercapto, oxo (=O), carboxy (COOH), nitro, pyrrolidinyl, piperidinyl, imidazolidinyl, imidazolinyl, piperazinyl, morpholinyl, thiomorpholinyl, and —$NR_fR_g$, wherein $R_f$ and $R_g$ may be the same or different and are chosen from hydrogen, $(C_1–C_6)$alkyl, and $(C_3–C_6)$cycloalkyl.

Specific and preferred values listed below for radicals, substituents, and ranges, are for illustration only; they do not exclude other defined values or other values within defined ranges for the radicals and substituents.

A specific value for X is N.
A specific value for X is CH.
A specific value for Y is N.
A specific value for Y is CH.
A specific value for $R_1$ is nitro.
A specific value for $R_1$ is hydrogen.
A specific value for $R_1$ is halo.
A specific value for $R_1$ is $(C_1–C_6)$alkoxy.
A specific value for $R_2$ is nitro.
A specific value for $R_2$ is hydrogen.
A specific value for $R_2$ is halo
A specific value for $R_2$ is $(C_1–C_6)$alkoxy.
A specific value for $R_1$ and $R_2$ taken together is methylenedioxy.

Specifically $R_3$ and $R_4$ are both nitro.
Specifically $R_3$ and $R_4$ are both halo.
Specifically $R_3$ and $R_4$ are both chloro.
Specifically $R_3$ and $R_4$ are both $(C_1–C_6)$alkoxy (e.g. methoxy).
Specifically one of $R_3$ and $R_4$ is hydrogen and the other is nitro.
Specifically one of $R_3$ and $R_4$ is hydrogen and the other is $(C_1–C_6)$alkoxy.
Specifically one of $R_3$ and $R_4$ is hydrogen and the other is halo.
Specifically one of $R_3$ and $R_4$ is hydrogen and the other is chloro.

A specific value for $R_3$ and $R_4$ taken together is methylenedioxy.

Specifically $R_1$ and $R_2$ taken together are methylenedioxy; and $R_3$ and $R_4$ are each methoxy.

Specifically $R_5$ is $(C_1–C_6)$alkoxycarbonyl, cyano, halo, hydroxy, mercapto, carboxy, nitro, pyrrolidinyl, piperidinyl, imidazolidinyl, imidazolinyl, piperazinyl, morpholinyl, thiomorpholinyl, or —$NR_fR_g$, wherein $R_f$ and $R_g$ may be the same or different and are chosen from hydrogen, $(C_1–C_6)$ alkyl, and $(C_3–C_6)$cycloalkyl.

Specifically $R_5$ is $(C_1–C_6)$alkoxycarbonyl, cyano, carboxy, or —$NR_fR_g$, wherein $R_f$ and $R_g$ may be the same or different and are chosen from hydrogen, $(C_1–C_6)$alkyl, and $(C_3–C_6)$cycloalkyl.

Specifically $R_5$ is —W-Z wherein: W is absent, —(C=O)—, —$CH_2$—, —(C=O)O—, —O(C=O)—, —O—, —$NR_a$(C=O)—, —C(=O)$NR_a$—, or —$NR_a$—; Z is $(C_1–C_4)$alkyl substituted with one or more water solubilizing groups; and $R_a$ is hydrogen or $(C_1–C_4)$alkyl.

A specific value for W is absent.
A specific value for W is —(C=O)—.
A specific value for W is —$CH_2$—.
A specific value for W is —(C=O)O—.
A specific value for W is —O(C=O)—.
A specific value for W is —O—.
A specific value for W is —$NR_a$(C=O)—.
A specific value for W is —C(=O)$NR_a$—.
A specific value for W is —$NR_a$—.

A specific value for Z is $(C_1–C_4)$alkyl substituted with one or two water solubilizing groups.
A specific value for Z is $(C_1–C_4)$alkyl substituted with one water solubilizing group.

A specific value for W is —O—.
A specific value for W is —NH—.

A specific value for Z is —$CH_2$—$R_a$ where $R_a$ is $(C_1–C_3)$ alkyl substituted with one or two water solubilizing groups.
A specific value for Z is —$CH_2$—$R_a$ where $R_a$ is $(C_1–C_3)$ alkyl substituted with one water solubilizing groups.

Specifically —W-Z is $(C_1–C_4)$alkyl substituted with one or more hydroxy groups.
Specifically —W-Z is $(C_1–C_4)$alkyl substituted with one hydroxy group.
Specifically —W-Z is $(C_1–C_4)$alkyl substituted with one or more mercapto groups.
Specifically —W-Z is $(C_1–C_4)$alkyl substituted with one mercapto group.
Specifically —W-Z is $(C_1–C_4)$alkyl substituted with one or more carboxy groups.
Specifically —W-Z is $(C_1–C_4)$alkyl substituted with one carboxy group.
Specifically —W-Z is $(C_1–C_4)$alkyl substituted with one or more $NR_fR_g$ groups; wherein $R_f$ and $R_g$ may be the same or different and are chosen from hydrogen, $(C_1–C_6)$alkyl, and $(C_3–C_6)$cycloalkyl.
Specifically —W-Z is $(C_1–C_4)$alkyl substituted with one $NR_fR_g$ group; wherein $R_f$ and $R_g$ may be the same or different and are chosen from hydrogen, $(C_1–C_6)$alkyl, and $(C_3–C_6)$cycloalkyl.
Specifically —W-Z is $(C_1–C_4)$alkyl substituted with one or more $NH_2$ groups.
Specifically —W-Z is a $(C_1–C_4)$alkyl substituted with one $NH_2$ group.
Specifically —W-Z is $(C_1–C_4)$alkyl substituted with one or more $N(CH_3)_2$ groups.

Specifically —W-Z is ($C_1$–$C_4$)alkyl substituted with one N($CH_3$)$_2$ group.

Specifically —W-Z is ($C_1$–$C_4$)alkyl substituted with one or more N($CH_2CH_3$)$_2$ groups.

Specifically —W-Z is ($C_1$–$C_4$)alkyl substituted with one N($CH_2CH_3$)$_2$ group.

Specifically —W-Z is ($C_1$–$C_4$)alkyl substituted with one or more ($C_1$–$C_6$)alkoxycarbonyl, cyano, halo, hydroxy, mercapto, oxo, carboxy, nitro, pyrrolidinyl, piperidinyl, imidazolidinyl, imidazolinyl, piperazinyl, morpholinyl, thiomorpholinyl, or —NR$_f$R$_g$ groups, wherein R$_f$ and R$_g$ may be the same or different and are chosen from hydrogen, ($C_1$–$C_6$)alkyl, and ($C_3$–$C_6$)cycloalkyl.

Specifically —W-Z is ($C_2$–$C_4$)alkyl substituted with one or two groups selected from hydroxy, mercapto, carboxy, amino, methylamino, ethylamino, dimethylamino, and diethylamino.

Specifically —W-Z is 2-hydroxyethyl.
Specifically —W-Z is 3-hydroxypropyl.
Specifically —W-Z is 2-hydroxypropyl.
Specifically —W-Z is —$CH_2CH_2$—NR$_f$R$_g$ wherein R$_f$ and R$_f$ are each independently hydrogen or ($C_1$–$C_6$)alkyl.

Specifically —W-Z is —$CH_2CH_2$—NR$_f$R$_g$ wherein R$_f$ and R$_f$ are each independently methyl or ethyl.

Specifically —W-Z is ($C_2$–$C_4$)alkoxy substituted with one or more hydroxy groups.

Specifically —W-Z is ($C_2$–$C_4$)alkoxy substituted with one hydroxy group.

Specifically —W-Z is ($C_2$–$C_4$)alkoxy substituted with one or more mercapto groups.

Specifically —W-Z is ($C_2$–$C_4$)alkoxy substituted with one mercapto group.

Specifically —W-Z is ($C_1$–$C_4$)alkoxy substituted with one or more carboxy groups.

Specifically —W-Z is ($C_1$–$C_4$)alkoxy substituted with one carboxy group.

Specifically —W-Z is ($C_2$–$C_4$)alkoxy substituted with one or more NR$_f$R$_g$ groups; wherein R$_f$ and R$_g$ may be the same or different and are chosen from hydrogen, ($C_1$–$C_6$)alkyl, and ($C_3$–$C_6$)cycloalkyl.

Specifically —W-Z is ($C_2$–$C_4$)alkoxy substituted with one NR$_f$R$_g$ group; wherein R$_f$ and R$_g$ may be the same or different and are chosen from hydrogen, ($C_1$–$C_6$)alkyl, and ($C_3$–$C_6$)cycloalkyl.

Specifically —W-Z is ($C_2$–$C_4$)alkoxy substituted with one or more $NH_2$ groups.

Specifically —W-Z is a ($C_2$–$C_4$)alkoxy substituted with one $NH_2$ group.

Specifically —W-Z is ($C_2$–$C_4$)alkoxy substituted with one or more N($CH_3$)$_2$ groups.

Specifically —W-Z is ($C_2$–$C_4$)alkoxy substituted with one N($CH_3$)$_2$ group.

Specifically —W-Z is ($C_2$–$C_4$)alkoxy substituted with one or more N($CH_2CH_3$)$_2$ groups.

Specifically —W-Z is ($C_2$–$C_4$)alkoxy substituted with one N($CH_2CH_3$)$_2$ group.

Specifically —W-Z is ($C_2$–$C_4$)alkoxy substituted with one or more ($C_1$–$C_6$)alkoxycarbonyl, cyano, halo, hydroxy, mercapto, oxo, carboxy, nitro, pyrrolidinyl, piperidinyl, imidazolidinyl, imidazolinyl, piperazinyl, morpholinyl, thiomorpholinyl, or —NR$_f$R$_g$ groups, wherein R$_f$ and R$_g$ may be the same or different and are chosen from hydrogen, ($C_1$–$C_6$)alkyl, and ($C_3$–$C_6$)cycloalkyl.

Specifically-W-Z is ($C_2$–$C_4$)alkoxy substituted with one or two groups selected from hydroxy, mercapto, carboxy, amino, methylamino, ethylamino, dimethylamino, and diethylamino.

Specifically —W-Z is 2-hydroxyethoxy.
Specifically —W-Z is 3-hydroxypropoxy.
Specifically —W-Z is 2-hydroxypropoxy.
Specifically —W-Z is —$OCH_2CH_2$—NR$_f$R$_g$ wherein R$_f$ and R$_f$ are each independently hydrogen or ($C_1$–$C_6$)alkyl.

Specifically —W-Z is —$OCH_2CH_2$—NR$_f$R$_g$ wherein R$_f$ and R$_f$ are each independently methyl or ethyl.

Specifically —W-Z is ($C_2$–$C_4$)alkylamino substituted with one or more hydroxy groups.

Specifically —W-Z is ($C_2$–$C_4$)alkylamino substituted with one hydroxy group.

Specifically —W-Z is ($C_2$–$C_4$)alkylamino substituted with one or more mercapto groups.

Specifically —W-Z is ($C_2$–$C_4$)alkylamino substituted with one mercapto group.

Specifically —W-Z is ($C_1$–$C_4$)alkylamino substituted with one or more carboxy groups.

Specifically —W-Z is ($C_1$–$C_4$)alkylamino substituted with one carboxy group.

Specifically —W-Z is ($C_2$–$C_4$)alkylamino substituted with one or more NR$_f$R$_g$ groups; wherein R$_f$ and R$_g$ may be the same or different and are chosen from hydrogen, ($C_1$–$C_6$)alkyl, and ($C_3$–$C_6$)cycloalkyl.

Specifically —W-Z is ($C_2$–$C_4$) alkylamino substituted with one NR$_f$R$_g$ group; wherein R$_f$ and R$_g$ may be the same or different and are chosen from hydrogen, ($C_1$–$C_6$)alkyl, and ($C_3$–$C_6$)cycloalkyl.

Specifically —W-Z is ($C_2$–$C_4$) alkylamino substituted with one or more $NH_2$ groups.

Specifically —W-Z is a ($C_2$–$C_4$) alkylamino substituted with one $NH_2$ group.

Specifically —W-Z is ($C_2$–$C_4$) alkylamino substituted with one or more N($CH_3$)$_2$ groups.

Specifically —W-Z is ($C_2$–$C_4$) alkylamino substituted with one N($CH_3$)$_2$ group.

Specifically —W-Z is ($C_2$–$C_4$) alkylamino substituted with one or more N($CH_2CH_3$)$_2$ groups.

Specifically —W-Z is ($C_2$–$C_4$) alkylamino substituted with one N($CH_2CH_3$)$_2$ group.

Specifically —W-Z is ($C_2$–$C_4$) alkylamino substituted with one or more ($C_1$–$C_6$)alkoxycarbonyl, cyano, halo, hydroxy, mercapto, oxo, carboxy, nitro, pyrrolidinyl, piperidinyl, imidazolidinyl, imidazolinyl, piperazinyl, morpholinyl, thiomorpholinyl, or —NR$_f$R$_g$ groups, wherein R$_f$ and R$_g$ may be the same or different and are chosen from hydrogen, ($C_1$–$C_6$)alkyl, and ($C_3$–$C_6$)cycloalkyl.

Specifically —W-Z is ($C_2$–$C_4$) alkylamino substituted with one or two groups selected from hydroxy, mercapto, carboxy, amino, methylamino, ethylamino, dimethylamino, and diethylamino.

Specifically —W-Z is 2-hydroxyethylamino.
Specifically —W-Z is 3-hydroxypropylamino.
Specifically —W-Z is 2-hydroxypropylamino.
Specifically —W-Z is —$NHCH_2CH_2$—NR$_f$R$_g$ wherein R$_f$ and R$_f$ are each independently hydrogen or ($C_1$–$C_6$)alkyl.

Specifically —W-Z is —$NHCH_2CH_2$—NR$_f$R$_g$ wherein R$_f$ and R$_f$ are each independently methyl or ethyl.

Specifically —W-Z is ($C_1$–$C_4$)alkanoyl substituted with one or more hydroxy groups.

Specifically —W-Z is ($C_1$–$C_4$)alkanoyl substituted with one hydroxy group.

Specifically —W-Z is ($C_1$–$C_4$)alkanoyl substituted with one or more mercapto groups.

Specifically —W-Z is ($C_1$–$C_4$)alkanoyl substituted with one mercapto group.

Specifically —W-Z is ($C_1$–$C_4$)alkanoyl substituted with one or more carboxy groups.

Specifically —W-Z is (C$_1$–C$_4$)alkanoyl substituted with one carboxy group.

Specifically —W-Z is (C$_1$–C$_4$)alkanoyl substituted with one or more NR$_f$R$_g$ groups; wherein R$_f$ and R$_g$ may be the same or different and are chosen from hydrogen, (C$_1$–C$_6$)alkyl, and (C$_3$–C$_6$)cycloalkyl.

Specifically —W-Z is (C$_1$–C$_4$)alkanoyl substituted with one NR$_f$R$_g$ group; wherein R$_f$ and R$_g$ may be the same or different and are chosen from hydrogen, (C$_1$–C$_6$)alkyl, and (C$_3$–C$_6$)cycloalkyl.

Specifically —W-Z is (C$_1$–C$_4$)alkanoyl substituted with one or more NH$_2$ groups.

Specifically —W-Z is a (C$_1$–C$_4$)alkanoyl substituted with one NH$_2$ group.

Specifically —W-Z is (C$_1$–C$_4$)alkanoyl substituted with one or more N(CH$_3$)$_2$ groups.

Specifically —W-Z is (C$_1$–C$_4$)alkanoyl substituted with one N(CH$_3$)$_2$ group.

Specifically —W-Z is (C$_1$–C$_4$)alkanoyl substituted with one or more N(CH$_2$CH$_3$)$_2$ groups.

Specifically —W-Z is (C$_1$–C$_4$)alkanoyl substituted with one N(CH$_2$CH$_3$)$_2$ group.

Specifically —W-Z is (C$_1$–C$_4$)alkanoyl substituted with one or more (C$_1$–C$_6$)alkoxycarbonyl, cyano, halo, hydroxy, mercapto, oxo, carboxy, nitro, pyrrolidinyl, piperidinyl, imidazolidinyl, imidazolinyl, piperazinyl, morpholinyl, thiomorpholinyl, or —NR$_f$R$_g$ groups, wherein R$_f$ and R$_g$ may be the same or different and are chosen from hydrogen, (C$_1$–C$_6$)alkyl, and (C$_3$–C$_6$)cycloalkyl.

Specifically —W-Z is (C$_2$–C$_4$)alkanloyl substituted with one or two groups selected from hydroxy, mercapto, carboxy, amino, methylamino, ethylamino, dimethylamino, and diethylamino.

Specifically —W-Z is 2-hydroxyethanoyl.

Specifically —W-Z is 3-hydroxypropanoyl.

Specifically —W-Z is 2-hydroxypropanoyl.

Specifically —W-Z is —C(O)CH$_2$CH$_2$—NR$_f$R$_g$ wherein R$_f$ and R$_f$ are each independently hydrogen or (C$_1$–C$_6$)alkyl.

Specifically —W-Z is —C(O)CH$_2$CH$_2$—NR$_f$R$_g$ wherein R$_f$ and R$_f$ are each independently methyl or ethyl.

Specifically —W-Z is (C$_1$–C$_4$)alkylaminocarbonyl substituted with one or more hydroxy groups.

Specifically —W-Z is (C$_1$–C$_4$)alkylaminocarbonyl substituted with one hydroxy group.

Specifically —W-Z is (C$_1$–C$_4$)alkylaminocarbonyl substituted with one or more mercapto groups.

Specifically —W-Z is (C$_1$–C$_4$)alkylaminocarbonyl substituted with one mercapto group.

Specifically —W-Z is (C$_1$–C$_4$)alkylaminocarbonyl substituted with one or more carboxy groups.

Specifically —W-Z is (C$_1$–C$_4$)alkylaminocarbonyl substituted with one carboxy group.

Specifically —W-Z is (C$_1$–C$_4$)alkylaminocarbonyl substituted with one or more NR$_f$R$_g$ groups; wherein R$_f$ and R$_g$ may be the same or different and are chosen from hydrogen, (C$_1$–C$_6$)alkyl, and (C$_3$–C$_6$)cycloalkyl.

Specifically —W-Z is (C$_1$–C$_4$)alkylaminocarbonyl substituted with one NR$_f$R$_g$ group; wherein R$_f$ and R$_g$ may be the same or different and are chosen from hydrogen, (C$_1$–C$_6$)alkyl, and (C$_3$–C$_6$)cycloalkyl.

Specifically —W-Z is (C$_1$–C$_4$)alkylaminocarbonyl substituted with one or more NH$_2$ groups.

Specifically —W-Z is (C$_1$–C$_4$)alkylaminocarbonyl substituted with one NH$_2$ group.

Specifically —W-Z is (C$_1$–C$_4$)alkylaminocarbonyl substituted with one or more N(CH$_3$)$_2$ groups.

Specifically —W-Z is (C$_1$–C$_4$)alkylaminocarbonyl substituted with one N(CH$_3$)$_2$ group.

Specifically —W-Z is (C$_1$–C$_4$)alkylaminocarbonyl substituted with one or more N(CH$_2$CH$_3$)$_2$ groups.

Specifically —W-Z is (C$_1$–C$_4$)alkylaminocarbonyl substituted with one N(CH$_2$CH$_3$)$_2$ group.

Specifically —W-Z is (C$_1$–C$_4$)alkylaminocarbonyl substituted with one or more (C$_1$–C$_6$)alkoxycarbonyl, cyano, halo, hydroxy, mercapto, oxo, carboxy, nitro, pyrrolidinyl, piperidinyl, imidazolidinyl, imidazolinyl, piperazinyl, morpholinyl, thiomorpholinyl, or —NR$_f$R$_g$ groups, wherein R$_f$ and R$_g$ may be the same or different and are chosen from hydrogen, (C$_1$–C$_6$)alkyl, and (C$_3$–C$_6$)cycloalkyl.

Specifically —W-Z is (C$_1$–C$_4$)alkylaminocarbonyl substituted with one or two groups selected from hydroxy, mercapto, carboxy, amino, methylamino, ethylamino, dimethylamino, and diethylamino.

Specifically —W-Z is 2-hydroxyethylaminocarbonyl.

Specifically —W-Z is 3-hydroxypropylaminocarbonyl.

Specifically —W-Z is 2-hydroxypropylaminocarbonyl.

Specifically —W-Z is —C(O)NHCH$_2$CH$_2$—NR$_f$R$_g$ wherein R$_f$ and R$_f$ are each independently hydrogen or (C$_1$–C$_6$)alkyl.

Specifically —W-Z is —C(O)NHCH$_2$CH$_2$—NR$_f$R$_g$ wherein R$_f$ and R$_f$ are each independently methyl or ethyl.

Specifically —W-Z is —NHC(O)CH$_2$CH$_2$—NR$_f$R$_g$ wherein R$_f$ and R$_f$ are each independently hydrogen or (C$_1$–C$_6$)alkyl.

Specifically —W-Z is —NHC(O)CH$_2$CH$_2$—NR$_f$R$_g$ wherein R$_f$ and R$_f$ are each independently methyl or ethyl.

A specific compound is a compound of formula I or II wherein R$_1$ and R$_2$ taken together are methylenedioxy; and R$_3$ and R$_4$ are each methoxy; or a pharmaceutically acceptable salt thereof.

A specific compound of the invention is a compound of formula I or II wherein the bond represented --- is a single bond.

A specific compound of the invention is a compound of formula I or II wherein the bond represented --- is a double bond.

A specific compound of the invention is a compound of formula I or formula II:

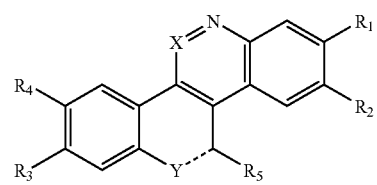

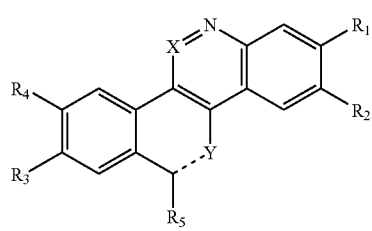

wherein:

the bond represented --- is a single bond or a double bond;

X is CH or N;

Y is CH or N when the bond represented --- is a double bond, or Y is CH$_2$ or NR$_a$ when the bond represented --- is a double bond;

one of R$_1$ and R$_2$ is nitro and the other is hydrogen, halo, or nitro; or R$_1$ and R$_2$ taken together are methylenedioxy;

one of R$_3$ and R$_4$ is nitro, halo, or (C$_1$–C$_6$)alkoxy and the other of R$_3$ and R$_4$ is hydrogen, nitro, halo, or (C$_1$–C$_6$)alkoxy;

R$_5$ is a solubilizing group; and

R$_a$ is hydrogen or (C—C$_6$)alkyl;

or a pharmaceutically acceptable salt thereof;

provided that Y is not N, when R$_5$ is —OH.

Another specific compound of the invention is a compound of the following formula:

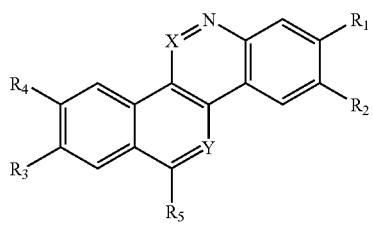

wherein:

X and Y are each independently CH or N;

one of R$_1$ and R$_2$ is nitro and the other is hydrogen, or nitro; or R$_1$ and R$_2$ taken together are methylenedioxy;

one of R$_3$ and R$_4$ is nitro, halo, or (C$_1$–C$_6$)alkoxy and the other of R$_3$ and R$_4$ is hydrogen, nitro, halo, or (C$_1$–C$_6$)alkoxy; and R$_5$ is a solubilizing group;

or a pharmaceutically acceptable salt thereof.

Another specific compound of the invention is a compound of the following formula:

wherein:

X and Y are each independently CH or N;

one of R$_1$ and R$_2$ is nitro and the other is hydrogen, or nitro; or R$_1$ and R$_2$ taken together are methylenedioxy;

one of R$_3$ and R$_4$ is nitro, halo, or (C$_1$–C$_6$)alkoxy and the other of R$_3$ and R$_4$ is hydrogen, nitro, halo, or (C$_1$–C$_6$)alkoxy; and R$_5$ is a solubilizing group;

or a pharmaceutically acceptable salt thereof.

A specific compound of the invention is a compound of formula III:

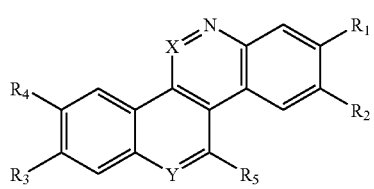

or a pharmaceutically acceptable salt thereof; wherein R$_1$–R$_5$, X and Y have any of the values or specific values defined herein.

A specific compound of the invention is a compound of IV:

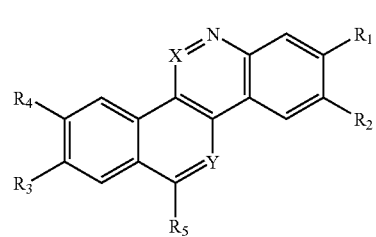

or a pharmaceutically acceptable salt thereof; wherein R$_1$–R$_5$, X and Y have any of the values or specific values defined herein.

A specific compound of the invention is a compound of formulas V:

V or a pharmaceutically acceptable salt thereof; wherein R$_1$–R$_5$, X and Y have any of the values or specific values defined herein.

A specific compound of the invention is a compound of formula VI.

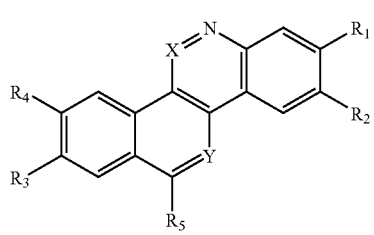

or a pharmaceutically acceptable salt thereof; wherein R$_1$–R$_5$

, X and Y have any of the values or specific values defined herein.

For a compound of formula I, II, III, and V when the bond represented by --- is a single bond, the additional valence on the carbon bearing $R_5$ that is not shown in the formula is occupied by a hydrogen.

A compound of formula I can be prepared, for example, as described in Schemes 1–4 below.

Typically, preferred compounds of the invention demonstrate some selectivity for Topoisomerase I compared to Topoisomerase II.

Representative compounds of formula I wherein: X is CH or N; Y is CH; W is C(=)O, C(=)OO; or $CH_2$; and Z is $N(CH_3)_2$, $CH_2N(CH_3)_2$, or $CH_2CH_2N(CH_3)_2$ can be prepared as illustrated in Scheme 1. Compounds 4, 5, 6, 9, 10, 11, 12 and 13 are representative compounds of formula 1.

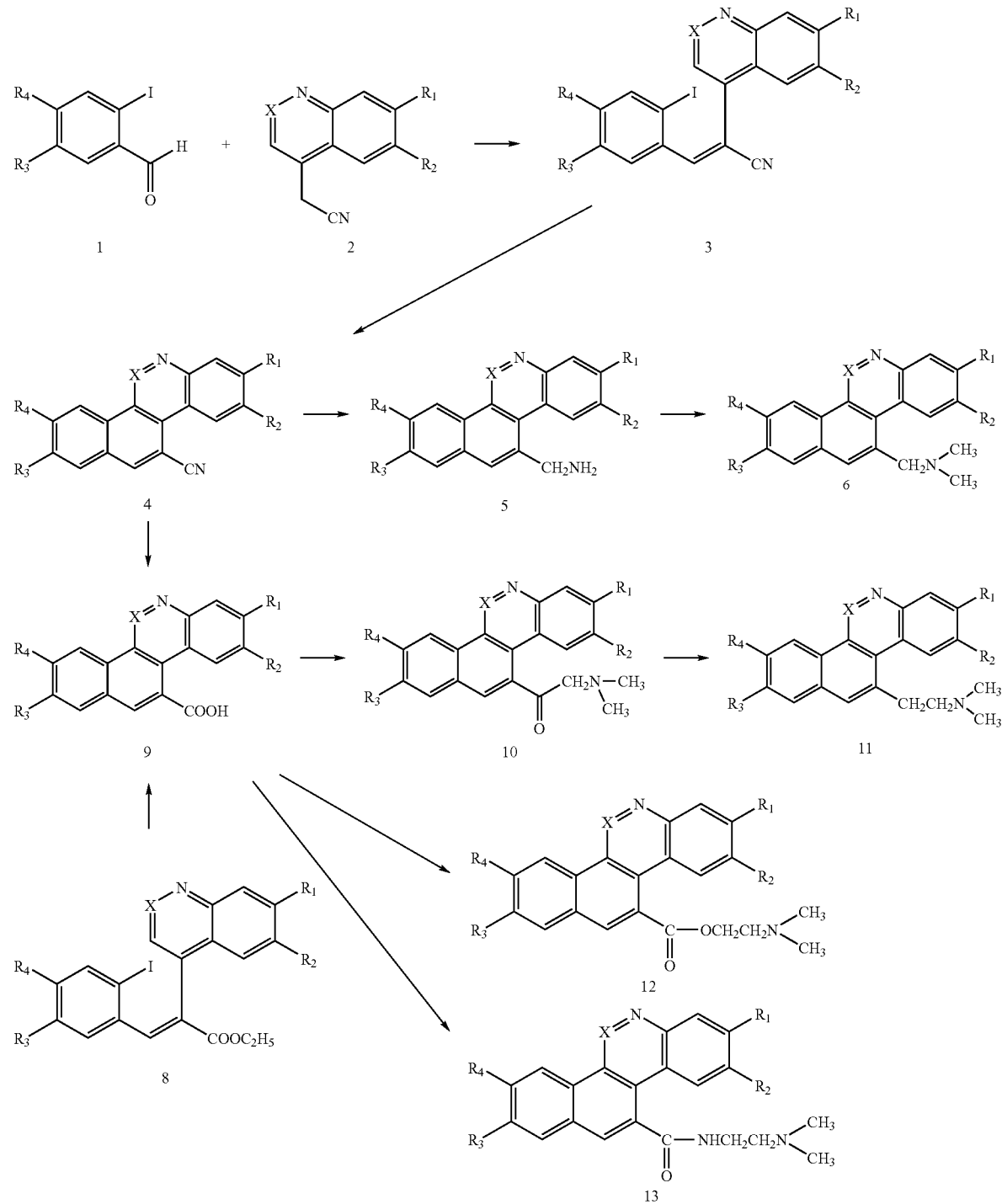

Scheme 1.

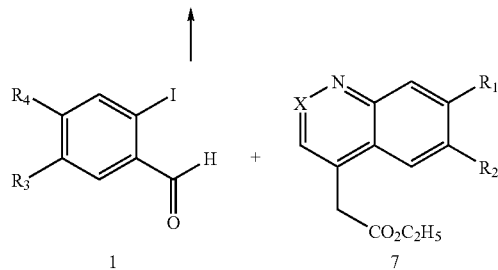

Condensation of the benzaldehyde 1 with the 4-quinolylacetonitrile 2 will provide 3, which in a palladium-catalyzed cyclization (or photo-initiated cyclization) will provide the cyano intermediate 4. Reduction of 4 will provide the benzylamine, 5, which can be converted to its N,N-dimethyl derivative, 6. The carboxylic acid 9 can be prepared by hydrolysis of 4. Alternatively, reaction of 1 and 7 will form 8, which upon palladium-catalyzed cyclization (or photo-initiated cyclization) followed by hydrolysis will form 9. Tin coupling performed by reacting N,N-dialkylaminomethyltributyl tin with the acid chloride of 9 will provide the α-dimethylaminoketone 10, which can be reduced to the 2-(N,N-dimethylaminoethyl) derivative, 11. Alternatively, the acid chloride of 9 can be reacted with various nucleophiles, such as N,N-dimethylethanolamine or N,N-dimethylethylenediamine to form the ester, 12, or amide, 13, respectively.

Representative compounds of formula I wherein X is CH or N; Y is CH; W is O or NH; and Z is $CH_2CH_2N(CH_3)_2$ can be prepared as illustrated in Scheme 2. Compounds 18, 19, 20, 21, 22, and 23 are representative compounds of formula I.

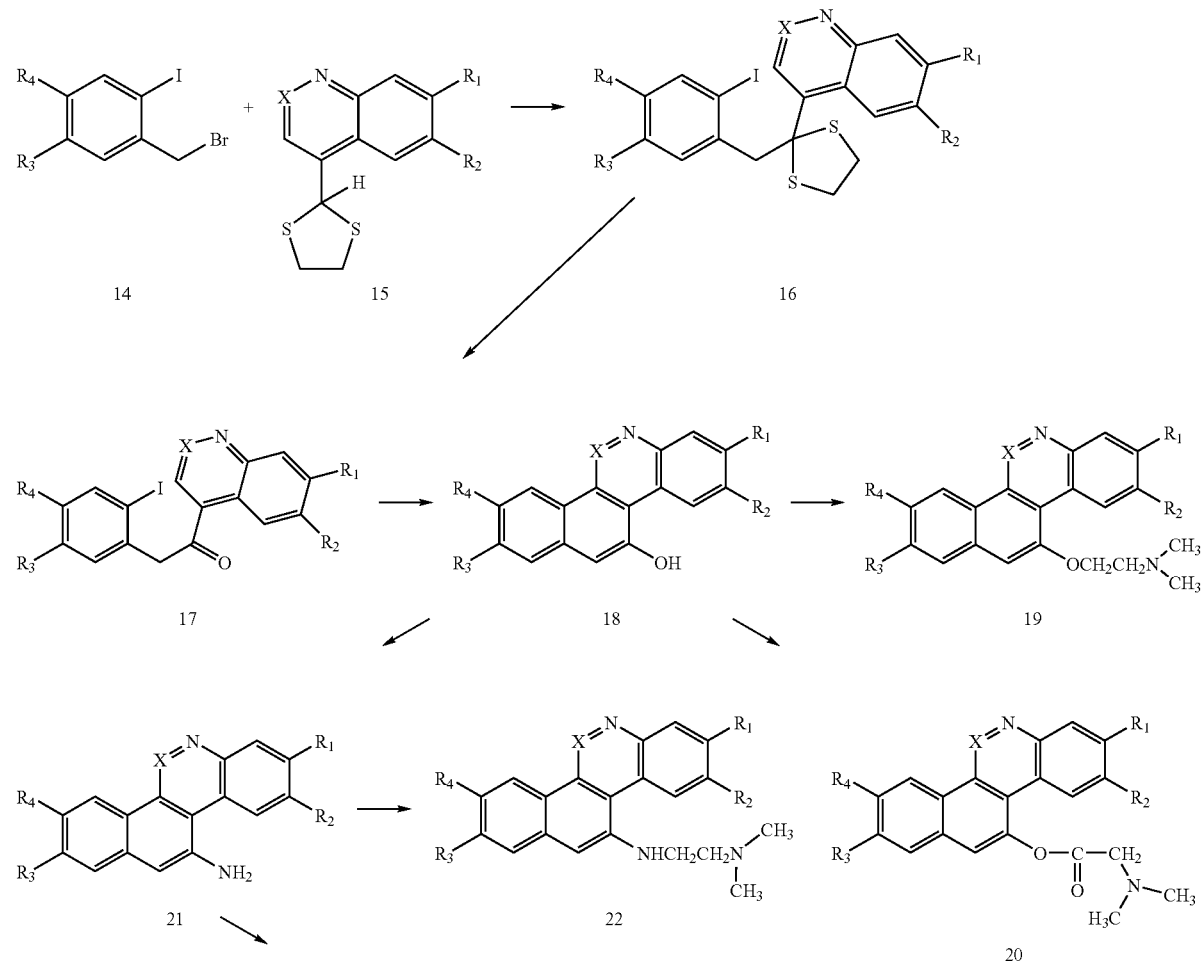

Scheme 2.

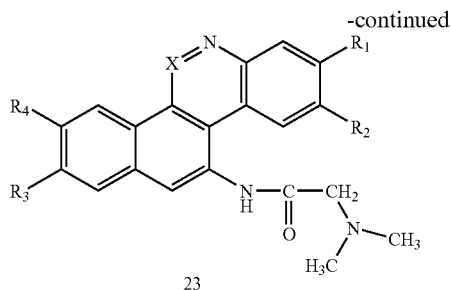

Reaction of the anion of the dithiane 15 with the benzyl bromide 14 will provide 16, which can be converted to the ketone 17. Palladium-catalyzed cyclization (or photo-initiated cyclization) of 17 will provide 18 which can be treated with a variety of electrophiles, including N,N-dimethyl-2-chloroethanamine which would provide 19. In addition, 18 could be acylated to provide the ester 20. Alternatively, 18 could be converted to the aryl amine 21, which could be similarly alkylated or acylated to provide 22 and 23, respectively.

Representative compounds of formula I wherein X is either CH or N; Y is N; W is CO, COO; or $CH_2$; and Z is $N(CH_3)_2$; $CH_2N(CH_3)_2$; $CH_2CH_2N(CH_3)_2$ can be prepared as illustrated in Scheme 3. Compounds 29, 30, 31, 32, 33, and 34 are representative compounds of formula I.

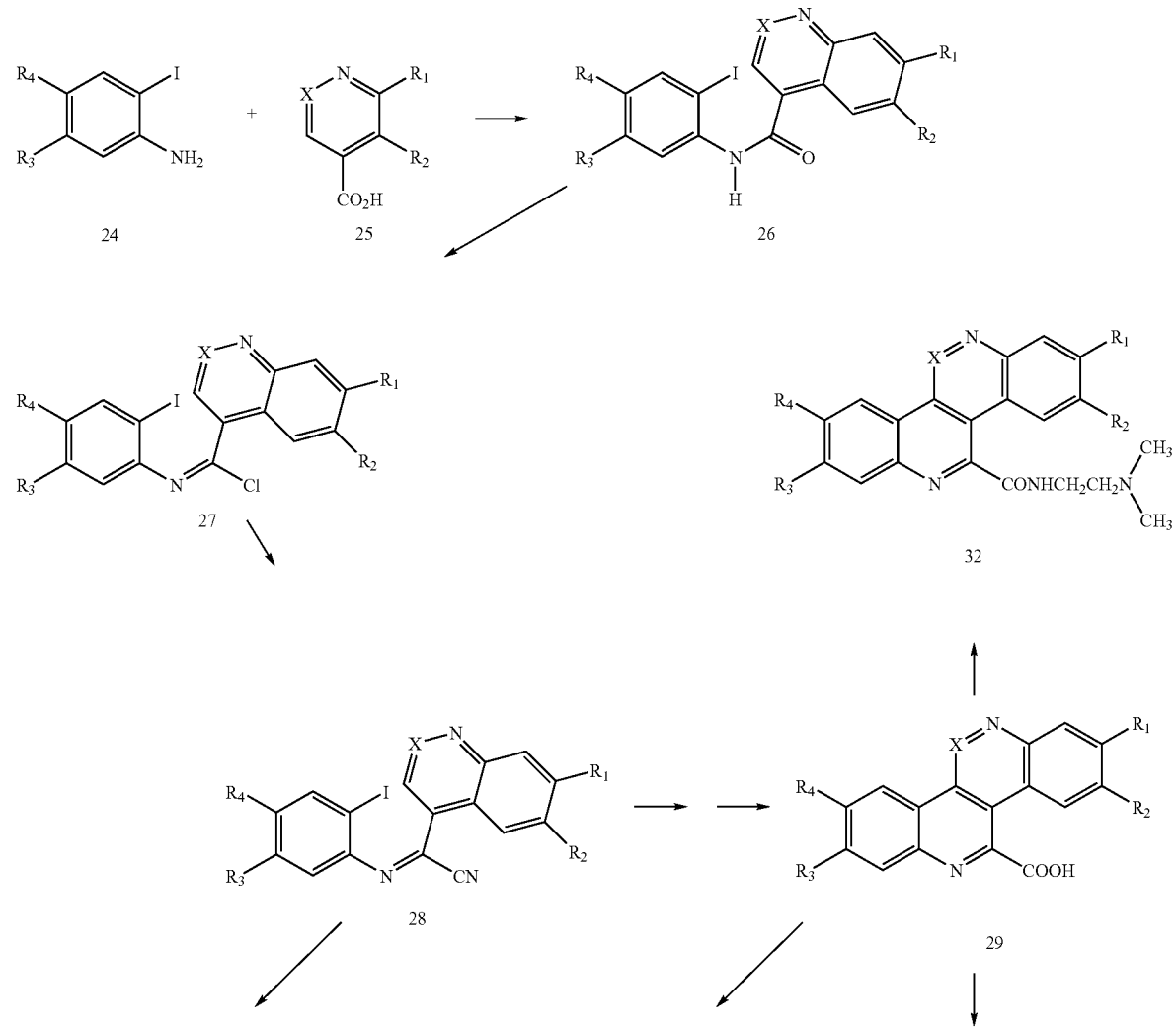

Scheme 3.

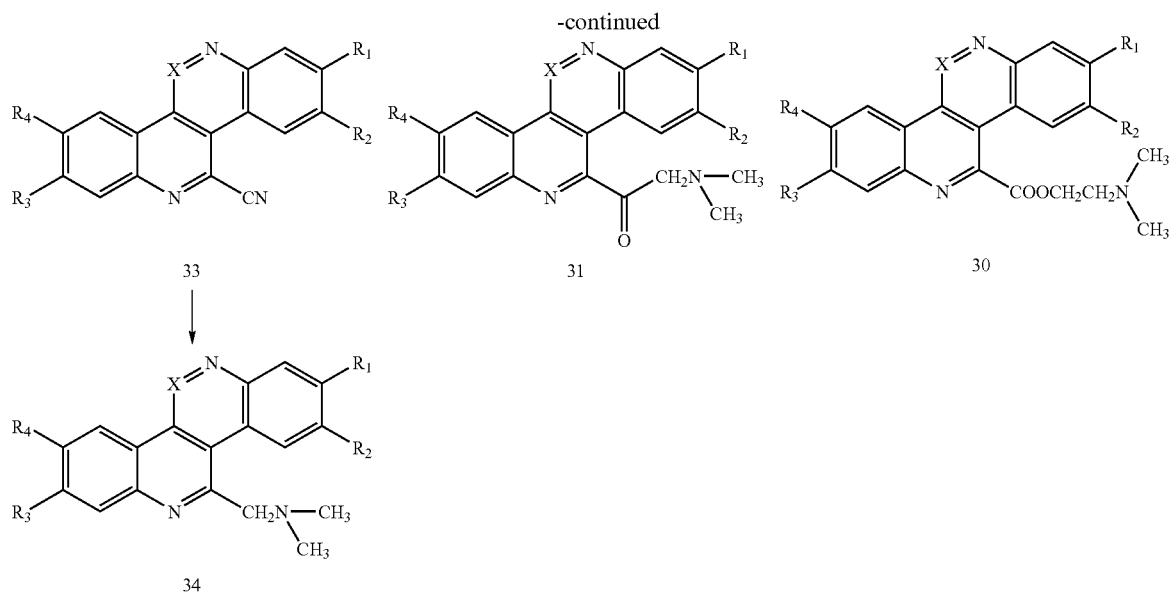

Reaction of 24 with the acid chloride of 25 will provide the amide 26, which in the presence of reagents such as phosphorous oxychloride will provide the chloro intermediate 27. Reaction of 27 with cyanide anion will provide 28, which can undergo palladium-catalyzed cyclization (or photo-initiated cyclization) and hydrolysis to give the acid 29. Treatment of the acid chloride of 29 with N,N-dialkylaminomethyltributyl tin will provide the α-aminoketone 31. Treatment of the acid chloride of 29 with 2-(N,N-dimethylamino)ethanol or N,N-dimethylethylenediamine will provide 30 and 32, respectively. Palladium-catalyzed cyclization (or photo-initiated cyclization) of 28 will provide 33. Reduction of 33 followed by methylation of the resulting amine will provide 34.

Representative compounds of formula I wherein X is CH or N; Y is N; W is O or NH; and Z is $CH_2CH_2N(CH_3)_2$ can be prepared as outlined in Scheme 4. Compounds 36, 39 and 40 are representative compounds of formula I.

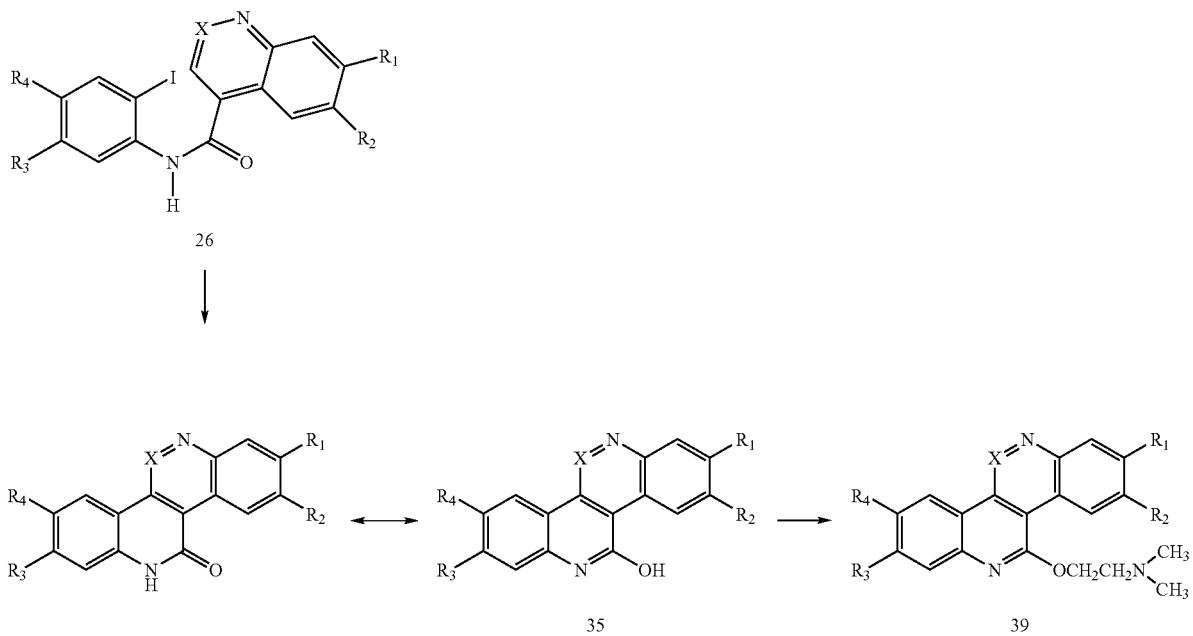

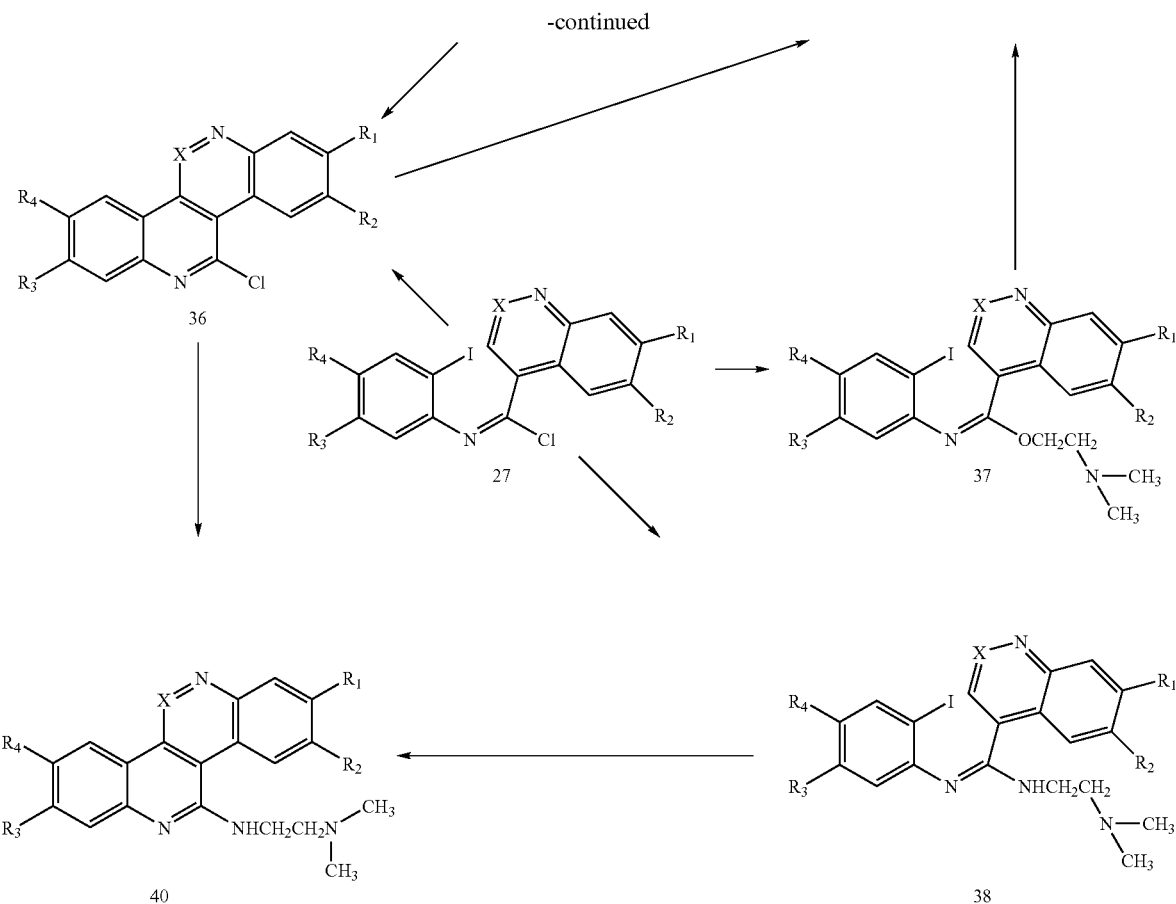

Scheme 4 illustrates three methods outlined for the preparation of compound 39. One involves direct alkylation of the enol form of compound 35. The second involves displacement of the chloro substituent on intermediate 36 with the alkoxide of 2-(N,N-dimethylamino)ethanol. The third alternative is to react 27 with 2-(N,N-dimethylamino)ethanol and to subject the resulting ether, 37, to palladium-catalyzed cyclization conditions (or photo-initiated cyclization). The two approaches to form 40 are similar. In one approach N,N-dimethylethylenediamine is reacted with 36. In the other N,N-dimethylethylenediamine is first reacted with 27 and the resulting product, 38, is subject to palladium-catalyzed cyclization conditions (or photo-initiated cyclization).

Representative compounds of formula II wherein: X is CH or N; Y is CH; W is CO, COO, or $CH_2$; and Z is $N(CH_3)_2$, $CH_2N(CH_3)_2$, or $CH_2CH_2N(CH_3)_2$ can be prepared as illustrated in Scheme 5. Compounds 104, 105, 106, 109, 110, 111, 112 and 113 are representative compounds of formula II.

Scheme 5.

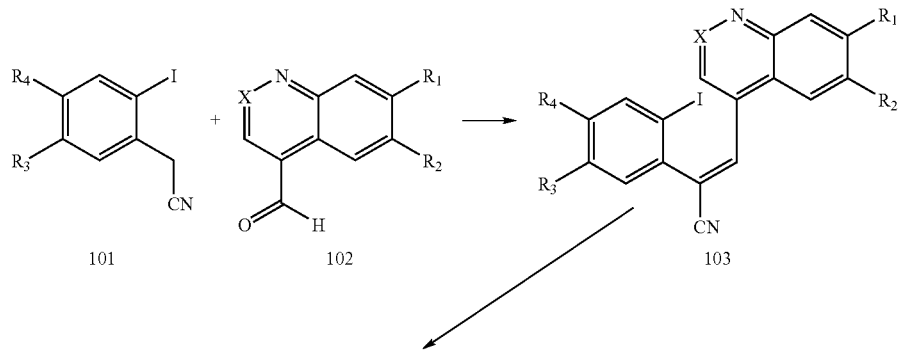

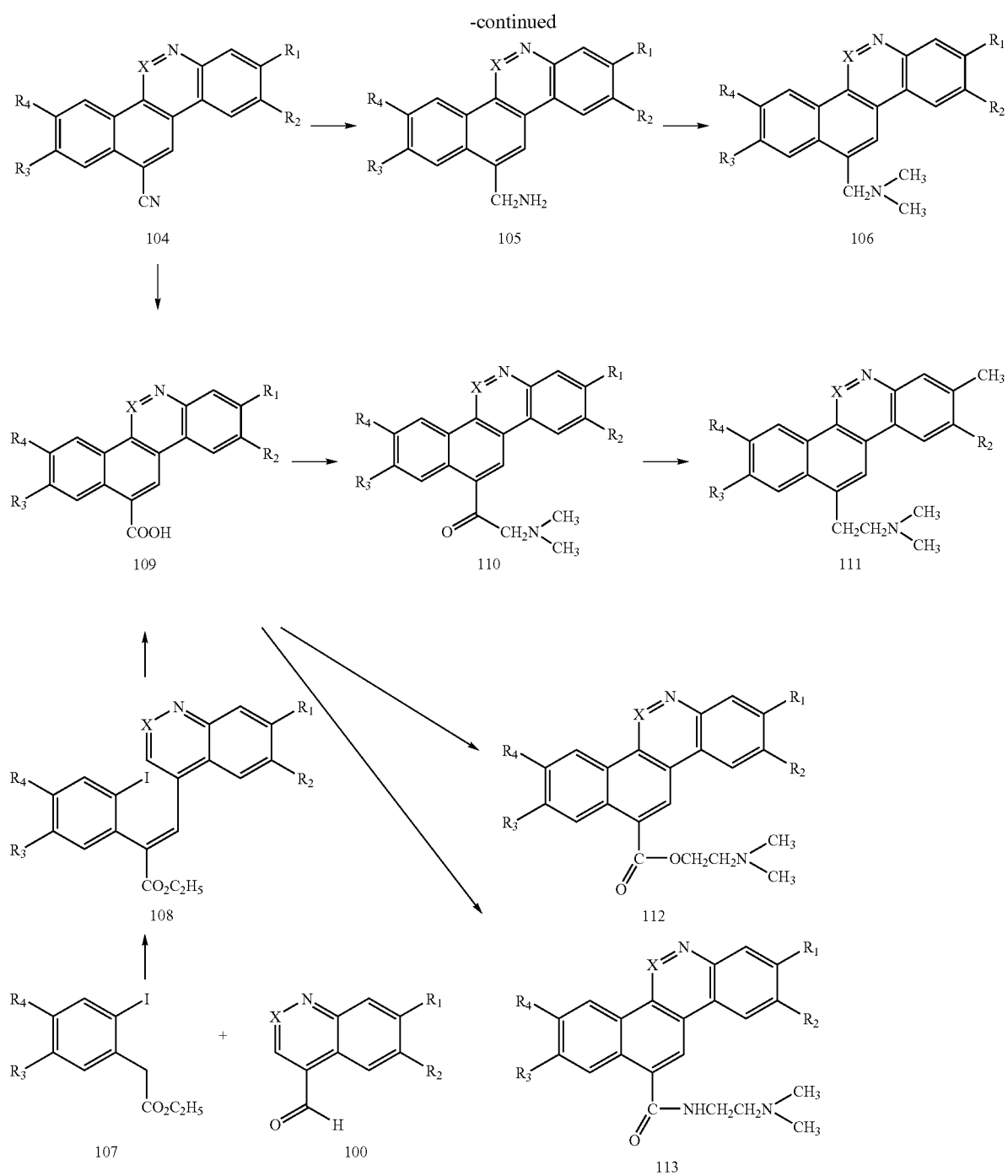

Condensation of the phenylacetonitrile 101 with 6,7-substituted 4-formylquinoline 102 will yield 103, which in a palladium-catalyzed cyclization (or photo-initiated cyclization) can be converted to the cyano intermediate 104. Reduction of 104 will provide the benzylamine, 105, which can be converted to its N,N-dimethyl derivative, 106. The carboxylic acid 109 can be prepared by hydrolysis of 104. Alternatively, reaction of 100 and 107 will form 108, which upon palladium-catalyzed cyclization (or photo-initiated cyclization) followed by hydrolysis will form 109. Tin coupling performed by reacting N,N-dialkylaminomethyl-tributyl tin with the acid chloride of 109 will provide the α-dimethylaminoketone 110, which can be reduced to the 2-(N,N-dimethylaminoethyl) derivative, 111. Alternatively, the acid chloride of 109 can be reacted with various nucleophiles, such as N,N-dimethylethanolamine or N,N-dimethylethylenediamine to form the ester, 112, or amide, 113, respectively.

Representative compounds of formula II wherein: X is CH or N; Y is CH; W is O or NH; and Z is $CH_2CH_2N(CH_3)_2$ can be prepared as outlined in Scheme 6. Compounds 118, 119, 120, 121, 122, and 123 are representative compounds of formula II.

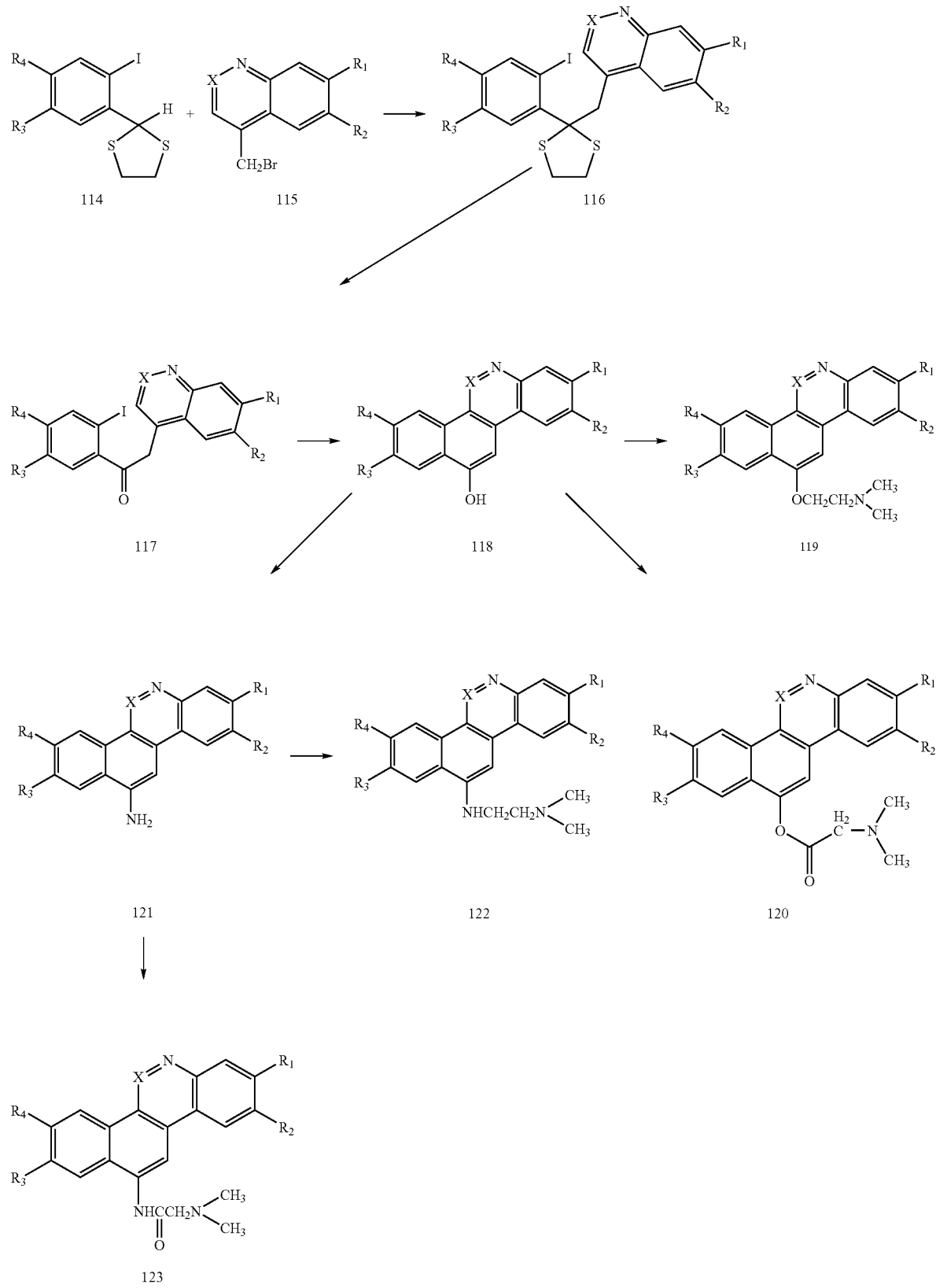
Scheme 6

Reaction of the anion of the dithiane 114 with the benzyl bromide 115 will provide 116, which can be converted to the ketone 117. Palladium-catalyzed cyclization of 117 (or photo-initiated cyclization) will provide 118 which can be treated with a variety of electrophiles, including N,N-dimethyl-2-chloroethanamine which would provide 119. In addition, it could be acylated to form 120. Alternatively, 118 could be converted to the aryl amine 121, which could be similarly alkylated or acylated to provide 122 and 123, respectively.

Representative compounds of formula II wherein: X is CH or N; Y is N; W is CO, COO, or $CH_2$; and Z is $N(CH_3)_2$, $CH_2N(CH_3)_2$, or $CH_2CH_2N(CH_3)_2$ can be prepared as outlined in Scheme 7. Compounds 129, 130, 131, 133, 132, 134 are representative compounds of formula II.

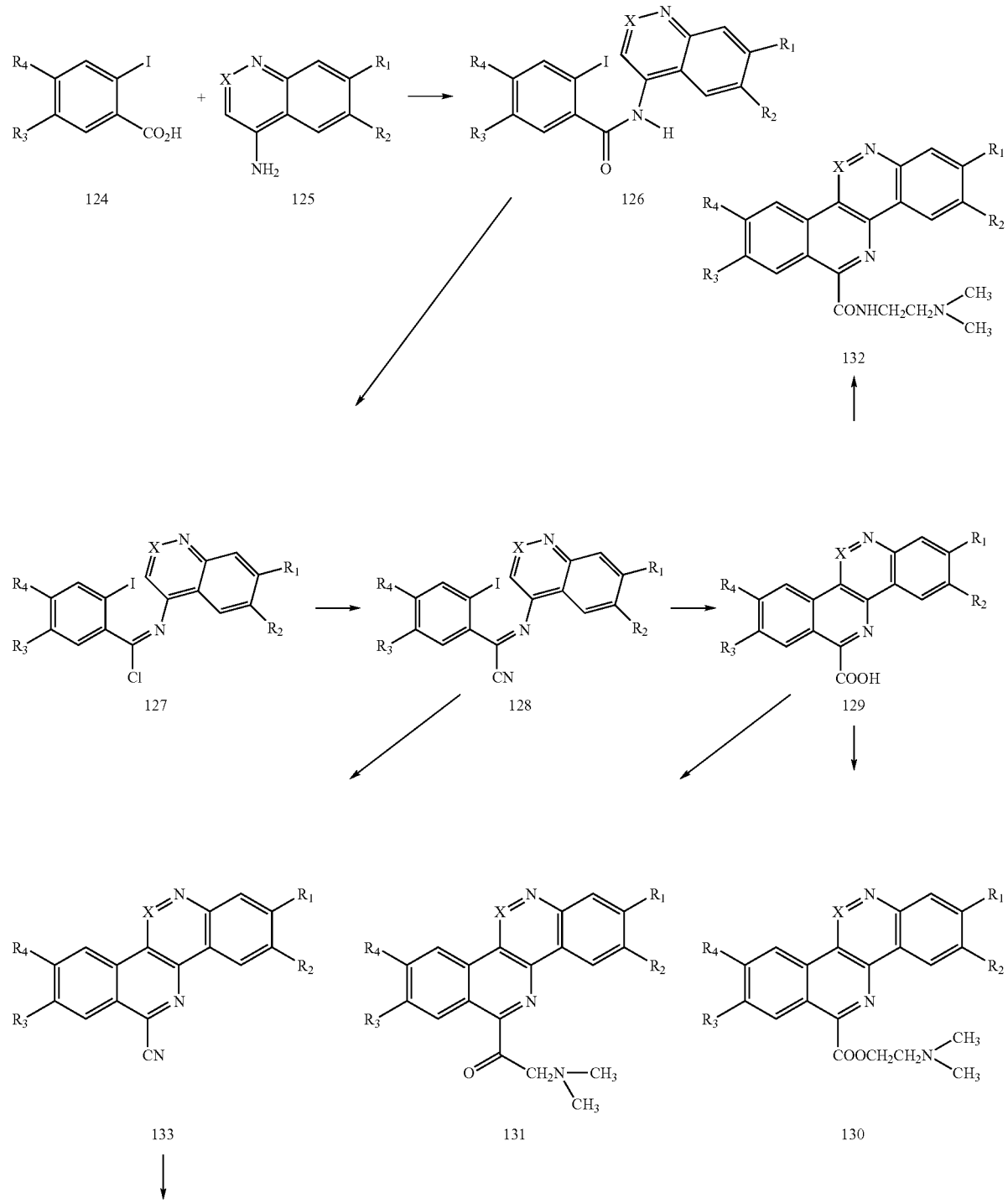

Scheme 7

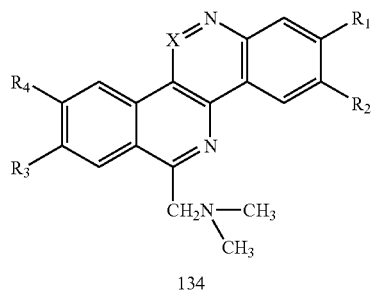

134

Reaction of 125 with the acid chloride of 124 will provide the amide 126, which in the presence of reagents such as phosphorous oxychloride will provide the chloro intermediate 27. Reaction of 127 with cyanide anion will provide 128, which can undergo palladium-catalyzed cyclization (or photo-initiated cyclization) and hydrolysis to give the acid 129. Treatment of the acid chloride of 129 with N,N-dialkylaminomethyltributyl tin will provide the α-aminoketone 131. Treatment of the acid chloride of 129 with 2-(N,N-dimethylamino)ethanol or N,N-dimethylaminethylenediamine will provide 130 and 132, respectively. Palladium-catalyzed cyclization of 128 (or photo-initiated cyclization) will provide 133. Reduction of 133 followed by methylation of the resulting amine will provide 134.

Representative compounds of formula II wherein: X is CH or N; Y is N; W is O or NH; and Z is $CH_2CH_2N(CH_3)_2$ can be prepared as illustrated in Scheme 8. Compounds 136, 139 and 140 are representative compounds of formula II.

Scheme 8.

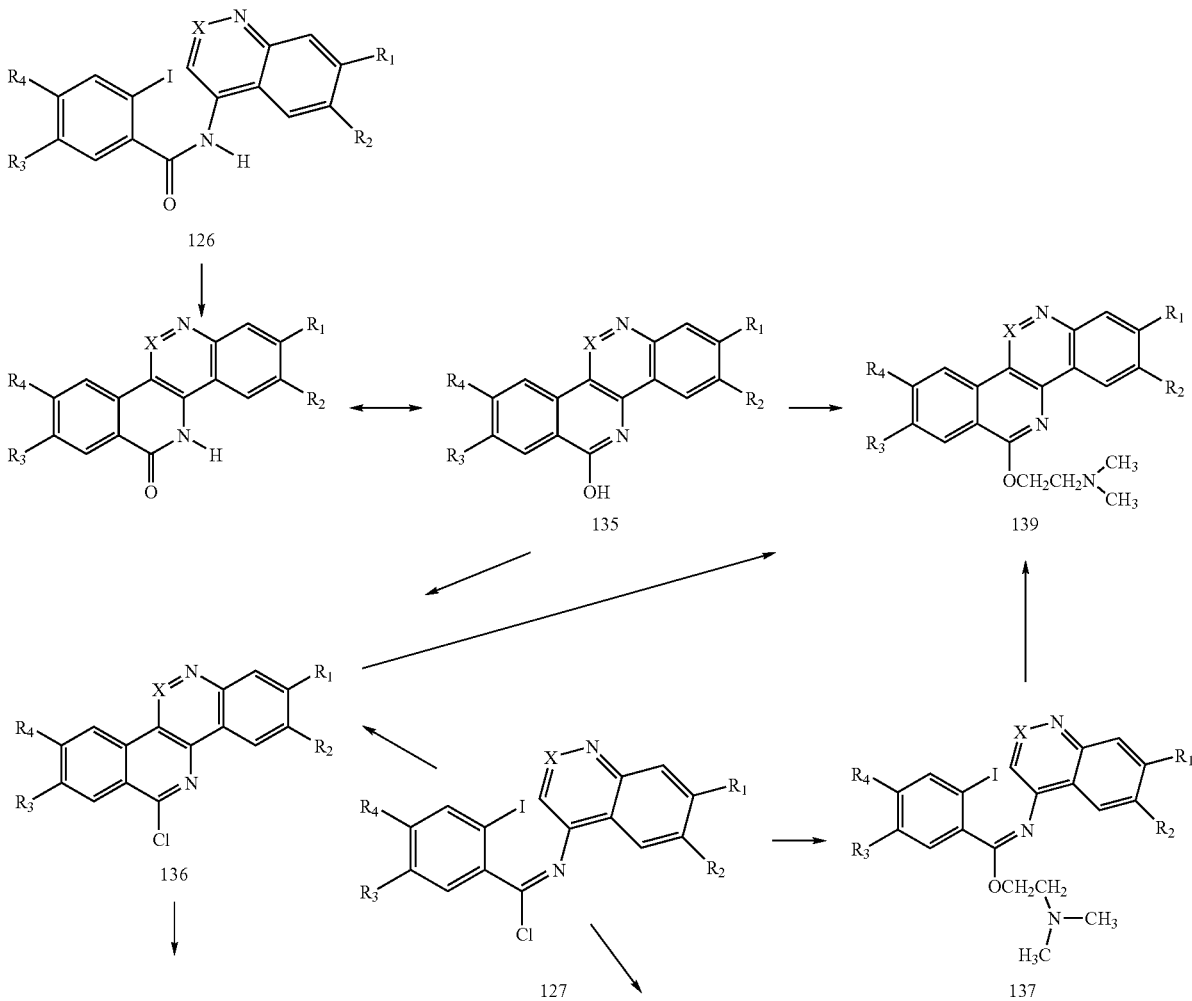

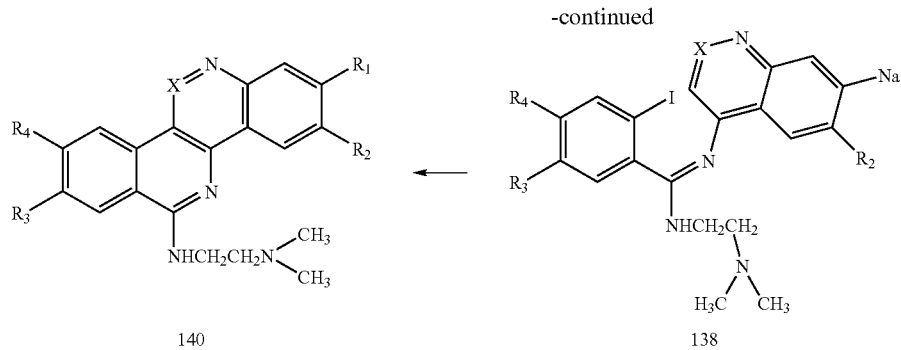

140    138

There are three methods outlined for the preparation of compound 139. One involves direct O-alkylation of compound 135. The second involves displacement of the chloro substituent on intermediate 136 with the alkoxide of 2-(N,N-dimethylamino)ethanol. The third alternative is to react 127 with 2-(N,N-dimethylamino)ethanol and to subject the resulting ether, 137, to palladium-catalyzed cyclization conditions (or photo-initiated cyclization). The two approaches to form 140 are similar. In one approach N,N-dimethylethylenediamine is reacted with 136. In the other N,N-dimethylethylenediamine is first reacted with 127 and the resulting product, 138, is subjected to palladium-catalyzed cyclization conditions (or photo-initiated cyclization).

Representative compounds of formula II wherein: X is CH or N; Y is $CH_2$; and the bond represented --- is a single bond can be prepared as illustrated in Scheme 9.

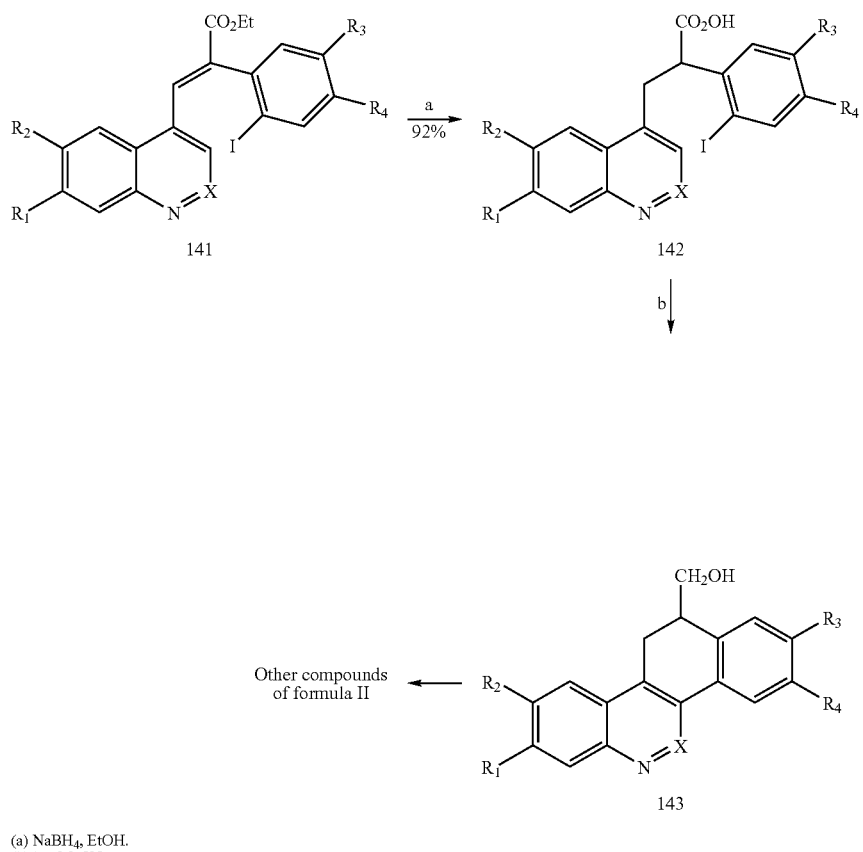

(a) $NaBH_4$, EtOH.
(b) hν, MeCN.

Reduction of ester 141 provides the alcohol 142. Palladium-catalyzed cyclization (or photo-initiated cyclization) of compound 142 provides the compound of the invention 143. Compound 143 is also a useful intermediate that can be used to prepare a variety of other compounds of the invention.

Representative compounds of formula I wherein: X is CH or N; Y is CH$_2$; and the bond represented --- is a single bond can be prepared as illustrated in Scheme 10.

how to determine topoisomerase inhibition activity or cytotoxic activity using the standard tests described herein, or using other similar tests which are well known in the art.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate,

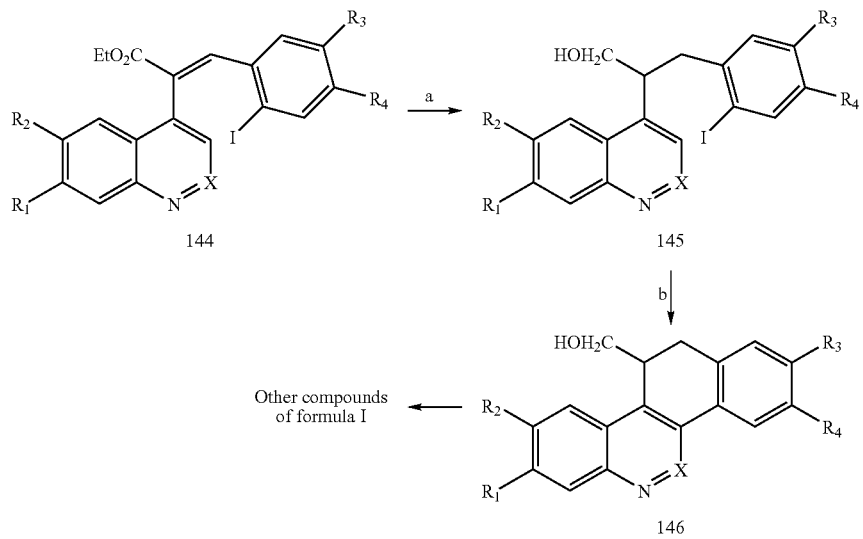

Scheme 10

(a) NaBH$_4$, EtOH.
(b) hν, MeCN.

Reduction of ester 144 provides the alcohol 145. Palladium-catalyzed cyclization (or photo-initiated cyclization) of compound 145 provides the compound of the invention 146. Compound 146 is also a useful intermediate that can be used to prepare a variety of other compounds of the invention.

The starting materials employed in the synthetic methods described herein are commercially available, have been reported in the scientific literature, or can be prepared from readily available starting materials using procedures known in the field. It may be desirable to optionally use a protecting group during all or portions of the above described synthetic procedures. Such protecting groups and methods for their introduction and removal are well known in the art. See Greene, T. W.; Wutz, P. G. M. "Protecting Groups In Organic Synthesis" second edition, 1991, New York, John Wiley & Sons, Inc.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal, for example, sodium, potassium or lithium, or alkaline earth metal, for example calcium, salts of carboxylic acids can also be made.

The compounds of formula I and II can be formulated as pharmaceutical compositions and administered to a mammalian host, such as a human patient in a variety of forms adapted to the chosen route of administration, that is, orally or parenterally, by intravenous, intramuscular, topical or subcutaneous routes.

Thus, the present compounds may be systemically administered, for example, orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the invention in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg per day, e.g., from about 1 to about 60 mg/kg of body weight per day or about 2 to 50 mg/kg per day.

The compound may conveniently be administered in unit dosage form; for example, containing 5 to 1,000 mg, conveniently 10 to 750 mg, most conveniently, 50 to 500 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to effect topoisomerase I or II mediated DNA cleavage can be determined using pharmacological models that are well known to the art, for example, using a model like Test A described below.

Test A. Topoisomerase-mediated DNA Cleavage Assays.

Human topoisomerase I was expressed in *E. Coli* and isolated as a recombinant fusion protein using a T7 expression system as described previously (Gatto, B., Sanders, M. M., Yu, C., Wu, H.-Y., Makhey, D., LaVoie, E. J., and Liu, L. F. (1996) *Cancer Res.* 56, 2795–2800). Recombinant human topoisomerase IIα was isolated and purified as previously described (Wasserman, R. A. Austin, C. A., Fisher, L. M.; Wang, J. C., *Cancer Res.*, 1993, 53, 3591; Halligan, B. D.; Edwards, K. A.; Liu, L. F. *J. Biol. Chem.* 1985, 260, 2475). Plasmid YepG was also purified by the alkali lysis method followed by phenol deproteination and CsCl/ethidium isopycnic centrifugation method as described. The end-labeling of the plasmid was accomplished by digestion with a restriction enzyme followed by end-filling with Klenow polymerase as previously described (Maniatis, T.; Fritsch, E. F.; Sambrook, *J. Molecular Cloning, a Laboratory Manual*; Cold Spring Harbor Laboratory: Cold Spring Harbor, N.Y. 1982; pp 149–185.). The cleavage assays were performed as previously reported (Gatto, B., Sanders, M. M., Yu, C., Wu, H.-Y., Makhey, D., LaVoie, E. J., and Liu, L. F. (1996) *Cancer Res.* 56, 2795–2800; Tewey, K. M., Rowe, T. C., Yang, L., Hallogan, B. C., and Liu, L. F. (1984) *Science* 226, 466–468; Li T-K., Chen A Y, Yu C, Mao Y, Wang H, Liu L F. (1999) Genes Dev 13(12): 1553–60; Wang, H.; Mao, Y.; Chen, A. Y.; Zhou, N.; and LaVoie, E. J.; Liu, L. F. *Biochemistry*, 2001, 40, 3316). The drug and the DNA in presence of topoisomerase I was incubated for 30 minutes at 37° C. After development of the gels, typically 24-hour exposure was used to obtain autoradiograms outlining the extent of DNA fragmentation. Topoisomerase I-mediated DNA cleavage values are reported as REC, Relative Effective Concentration, i.e. concentrations relative to topotecan, whose value is arbitrarily assumed as 1.0, that are able to produce the same cleavage on the plasmid DNA in the presence of human topoisomerase I. Topoisomerase II-mediated DNA cleavage values are reported as REC, Relative Effective Concentration, potency was based upon the relative amount of drug needed to induce approximately 10% DNA fragmentation, i.e. concentrations relative to VM-26, whose value is arbitrarily assumed as 1.0, that are able to produce the same cleavage on the plasmid DNA in the presence of human topoisomerase II. The relative effective concentration (REC) values as compared to camptothecin that results in approximately 10% cleavage of DNA for representative compounds of the invention are typically in the range of from about 0.1 to about 100.

The cytotoxic effects of a compound of the invention can be determined using pharmacological models that are well known to the art, for example, using a model like Test B described below.

Test B. Inhibition of Cell Growth: MTT-Microtiter Plate Tetrazolinium Cytotoxicity Assay (RPMI 8402, CPT-K5, U937, U937/CR Cells)

The cytotoxicity is determined using the MTT-microfiter plate tetrazolinium cytotoxicity assay (MTA), see Chen A. Y. et al. *Cancer Res.* 1993, 53, 1332; Mosmann, T. J., *J. Immunol. Methods* 1983, 65, 55; and Carmichael, J. et al. *Cancer Res.* 1987, 47, 936. The human lymphoblast RPMI 8402 and its camptothecin-resistant variant cell line, CPT-K5 were provided by Dr. Toshiwo Andoh (Anchi Cancer Research Institute, Nagoya, Japan), see Andoh, T.; Okada, K, *Adv. in Pharmacology* 1994, 29B, 93. Human U-937 myeloid leukemia cells and U-937/CR cells were described by Rubin et al., *J. Biol. Chem.*, 1994, 269, 2433–2439. The cytotoxicity assay is performed by using 96-well microtiter plates using 2000 cells/well, in 200 mL of growth medium. Cells are grown in suspension at 37° C. in 5% $CO_2$ and maintained by regular passage in RPMI medium supplemented with 10% heat-inactivated fetal bovine serum, L-glutamine (2 mM), penicillin (100 U/mL), and streptomycin (0.1 mg/mL). For determination of $IC_{50}$, cells are exposed continuously for 3–4 days to varying concentrations of drug, and MTT assays were performed at the end of the fourth day. Each assay is performed with a control that did not contain any drug. All assays are performed at least twice in 6 replicate wells. All assays are performed under the direction of Dr. L. F. Liu, Department of Pharmacology, The University of Medicine and Dentistry of New Jersey, Robert Wood Johnson Medical School, Piscataway, N.J. Representative compounds of the invention typically demonstrate an $IC_{50}$ of less than 1 micromolar in this assay.

The compounds of the invention can function as cytotoxic agents against tumor cell lines, including multi-drug resistant tumor cell lines. Thus, the compounds are useful to treat cancer and can be used to treat tumors that are resistant to other specific chemotherapeutic agents.

Topoisomerase inhibitors are also known to possess antibacterial, antifungal, antiprotozoal, antihelmetic, and antiviral activity. Accordingly, the topoisomerase inhibitors of the invention may also be useful as antibacterial, antifungal, antipsoritic (psoriasis) antiprotozoal, antihelmetic, or antiviral agents. In particular, compounds of the invention that demonstrate little or no activity as mammalian topoisomerase I poisons, because of the possibility of similar molecular mechanism of action, could be highly active and selective antibacterial, antifungal, antiprotozoal, antihelmetic, or antiviral agents. Thus, certain compounds of the invention may be particularly useful as systemic antibacterial, antifungal, antiprotozoal, antihelmetic, or antiviral agents in mammals. The invention also provides the use of a compound of the invention for the manufacture of a medicament useful for producing an antibacterial, antifungal, antiprotozoal, antihelmetic, or antiviral effect in a mammal.

As used herein, the term "solid mammalian tumors" include cancers of the head and neck, lung, mesothelioma, mediastinum, esophagus, stomach, pancreas, hepatobiliary system, small intestine, colon, rectum, anus, kidney, ureter, bladder, prostate, urethra, penis, testis, gynecological organs, ovarian, breast, endocrine system, skin central nervous system; sarcomas of the soft tissue and bone; and melanoma of cutaneous and intraocular origin. The term "hematological malignancies" includes childhood leukemia and lymphomas, Hodgkin's disease, lymphomas of lymphocytic and cutaneous origin, acute and chronic leukemia, plasma cell neoplasm and cancers associated with AIDS. The preferred mammalian species for treatment are humans and domesticated animals.

The invention will now be illustrated by the following non-limiting Examples.

EXAMPLES
Representative compounds of the invention were prepared as illustrated below in Schemes A–C.
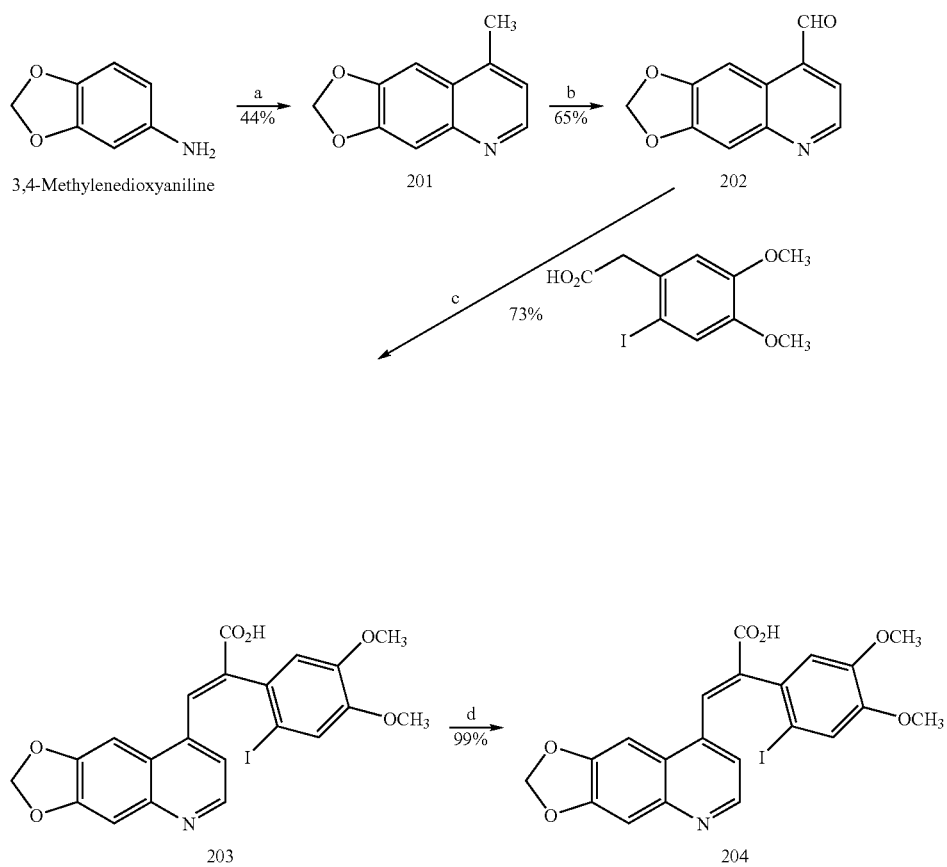
(a) methyl vinyl ketone, FeCl$_3$, AcOH.
(b) SeO$_2$, dioxane, H$_2$O.
(c) Ac$_2$O, TEA.
d) SOCl$_2$, EtOH.

Scheme B

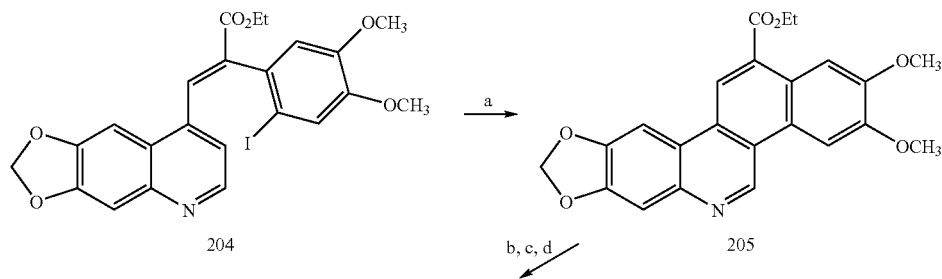

(a) hν, MeCN.
(b) NaOH, H₂O, EtOH.
(c) SOCl₂.
(d) N,N-dimethylethylenediamine

Example 1

Synthesis of Compound 205

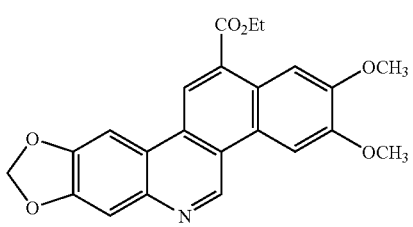

A solution of compound 204 (450 mg, 0.85 mmol) in acetonitrile (800 mg) was transferred to the photoreactor apparatus and was degassed by nitrogen purge for 30 minutes. The solution was then irradiated through a vycor filter for 45 minutes. The mixture was removed from the photoreactor, and an equal portion of compound 204 (450 mg, 0.85 mmol) in acetonitrile (800 mg) was reacted according to the same procedure. The cyclized product, which had precipitated out during the course of the reaction, was isolated by filtration and was washed with additional acetonitrile. Thorough drying yielding 348 mg, in 51% yield; $^1$H NMR (CDCl₃+1 drop CD₃OD) δ 1.48 (t, 3H, J=7.1), 3.98 (s, 3H), 4.13 (s, 3H), 4.53 (q, 2H, J=7.1), 6.26 (s, 2H), 7.73 (s, 1H), 7.93 (s, 1H), 8.11 (s, 1H), 8.18 (s, 1H), 8.70 (s, 1H), 10.24 (s, 1H); $^{13}$C NMR (CDCl₃+1 drop CD₃OD) δ 14.2, 55.9, 56.6, 62.5, 99.5, 100.0, 102.9, 103.8, 106.6, 120.4, 121.2, 123.2, 124.7, 126.8, 131.8, 132.7, 135.0, 139.8, 151.4, 151.5, 152.3, 152.4, 166.7; HRMS calcd for C₂₃H₁₉NO₆H: 406.1290; found 406.1270.

The intermediate compound 204 was prepared as follows.

a. Synthesis of compound 201. Iron (III) chloride (54.2 g, 0.33 mol) was dissolved in glacial acetic acid (600 mL) with warming to 60° C. 3,4-Methylenedioxyaniline (27.4 g, 0.2 mol) was added and the mixture was stirred for 5 minutes. Methyl vinyl ketone (17.4 mL, 0.21 mol) was added dropwise over five minutes. Following the completion of the addition, the mixture was heated to reflux with stirring for 1.5 hours. The mixture was cooled and the precipitate was filtered and washed with additional acetic acid. This material was then neutralized by addition to cold 30% NaOH, and the resulting mixture was filtered and air-dried. The crude material was then extracted with chloroform (7×200 mL), and the combined extracts were washed with 10% $K_2CO_3$ (3×300 mL) and were dried ($MgSO_4$) and concentrated under vacuum. The resulting material was recrystallized from ethyl ether, yielding 16.6 g as a fluffy light beige solid, in 44% yield; mp 100.5–101.5° C.; $^1H$ NMR ($CDCl_3$) δ 2.51 (s, 3H), 6.04 (s, 2H), 7.02 (d, 1H, J=4.4), 7.13 (s, 1H), 7.32 (s, 1H), 8.52 (d, 1H, J=4.4); $^{13}C$ NMR ($CDCl_3$) δ 19.1, 99.3, 101.7, 106.3, 120.6, 125.0, 142.9, 146.3, 147.8, 147.9, 150.2; HRMS calcd for $C_{11}H_9O_2N$: 187.0633; found: 187.0627.

b. Synthesis of compound 202. A mixture of compound 201 (5.01 g, 27.0 mmol) in 30 mL dioxane was heated to 75° C., and then a solution of $SeO_2$ in 5:1 dioxane-$H_2O$ (36 mL) was added dropwise. The mixture was heated to reflux with stirring for 4.5 h, and was filtered and the filtrate was evaporated. The residue was dissolved in chloroform (50 mL) and washed with water (3×50 mL), dried ($MgSO_4$) and evaporated. The residue was chromatographed, eluting with $CHCl_3$, yielding 3.48 g, in 65% yield; mp 146.0–147.5° C.; IR ($CHCl_3$) 1702; $^1H$ NMR ($CDCl_3$) δ 6.18 (s, 2H), 7.45 (s, 1H), 7.63 (d, 1H, J=4.4), 8.41 (s, 1H), 8.96 (d, 1H, J=4.4), 10.35 (s, 1H); $^{13}C$ NMR ($CDCl_3$) δ 100.4, 102.3, 106.3, 121.4, 124.7, 135.7, 148.0, 148.3, 150.8, 151.0, 193.4; HRMS calcd for $C_{11}H_7NO_3$: 201.0426; found 201.0437.

c. Synthesis of compound 203. A mixture of compound 202 (400 mg, 2.0 mmol) and 2-iodo-4,5-dimethoxyphenylacetic acid (966 mg, 3.0 mmol, Qandil, A. M., Synthesis, 1999, 2033–2035) in acetic acid (3.5 mL) and TEA (0.31 mL) was heated to reflux with stirring for 90 min. The mixture was cooled to about 70° C., was poured into water, and the resulting mixture was stirred for 30 min with no additional heating. The entire mixture was then evaporated under vacuum and the residue was chromatographed eluting with 97:3 chloroform-methanol, to provide 725 mg, in 73% yield; $^1H$ NMR (DMSO-$d_6$) δ 3.47 (s, 3H), 3.72 (s, 3H), 6.24 (s, 2H), 6.67 (s, 1H), 6.83 (d, 1H, J=4.7), 7.23 (s, 1H), 7.33 (s, 1H), 7.41 (s, 1H), 8.15 (s, 1H), 8.44 (d, 1H, J=4.7); HRMS calcd for $C_{21}H_{61}INO6H$: 506.0101; found: 506.0110.

d. Synthesis of compound 204. Thionyl chloride (5 mL) was added dropwise to a mixture of compound 203 (1.51 g, 3.0 mmol) in absolute ethanol (125 mL), and the mixture was refluxed for 5 h with stirring. The mixture was cooled and evaporated under vacuum. The residue was dissolved in chloroform (250 mL) and washed with sat. $NaHCO_3$ (3×250 mL), dried, evaporated, and chromatographed eluting with chloroform, to provide 1.59 g, in 99% yield, as an orange oil; $^1H$ NMR ($CDCl_3$) δ 1.31 (t, 3H, J=7.0), 3.47 (s, 3H), 3.80 (s, 3H), 4.31 (q, 2H, J=7.0), 6.07 (d, 2H), 6.39 (s, 1H), 6.71 (d, 1H, J=4.6), 7.18 (s, 1H), 7.29 (s, 2H), 8.20 (s, 1H), 8.38 (d, 1H, J=4.6); $^{13}C$ NMR ($CDCl_3$) δ 14.3, 55.9, 56.1, 61.8, 88.2, 99.6, 102.0, 106.4, 113.5, 119.1, 121.4, 123.6, 132.4, 136.4, 139.2, 140.2, 146.8, 147.5, 148.5, 149.3, 150.6, 166.0; HRMS calcd for $C_{23}H_{21}NO_6H$: 533.0413; found 533.0419.

Example 2

Synthesis of Compound 206.

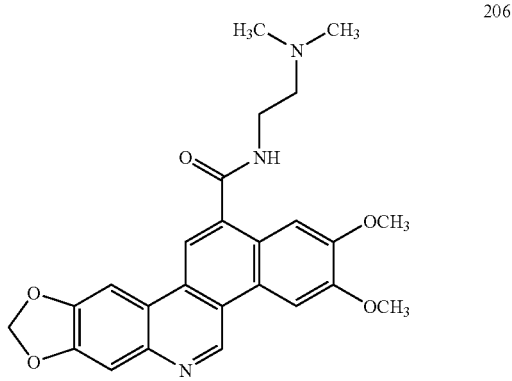

A mixture of compound 205 (40 mg, 0.1 mmol) in 10% NaOH (45 mL) and ethanol (10 mL) was heated to reflux with stirring overnight. The mixture was concentrated to dryness and water (30 mL) was added. The resulting mixture was acidified by the addition of acetic acid and the free acid was then isolated by filtration. After complete drying, 32 mg (87%) was obtained. This acid was added to thionyl chloride and the mixture was heated to reflux for 4 h. The excess thionyl chloride was removed under vacuum, and N,N-dimethylethylenediamine (5 mL) was added, and the mixture was stirred at ambient temperature for 30 minutes. The N,N-dimethylethylenediamine was evaporated and the residue was dissolved in chloroform (25 mL) and washed with sat. $NaHCO_3$ (3×25 mL), and extracted into dilute aqueous HCl (3×25 mL). The combined aqueous extracts were washed with chloroform (2×25 mL), were basified (30% NaOH), and back-extracted into ethyl acetate (3×30 mL). The organic phases were dried ($MgSO_4$) and evaporated, and the residue was chromatographed eluting with 96:4 chloroform-methanol, providing 18 mg, in 52% yield; $^1H$ NMR ($CDCl_3$+1 drop $CD_3OD$) δ 2.34 (s, 6H), 2.69 (t, 2H, J=6.2), 3.70 (t, 2H, J=6.2), 4.01 (s, 3H), 4.10 (s, 3H), 6.11 (s, 2H), 7.35 (s, 1H), 7.75 (s, 1H), 7.79 (s, 1H), 7.93 (s, 1H), 8.29 (s, 1H), 9.59 (s, 1H); $^{13}C$ NMR ($CDCl_3$+1 drop $CD_3OD$) δ 37.5, 45.2, 55.9, 56.0, 58.3, 99.3, 102.0, 102.1, 106.2, 106.3, 117.7, 120.8, 120.9, 123.9, 125.7, 129.6, 136.1, 141.6, 144.7, 148.7, 149.6, 149.9, 150.6, 170.0; HRMS calcd for $C_{25}H_{25}N_3O_5H$: 448.1872; found 448.1865.

Scheme C

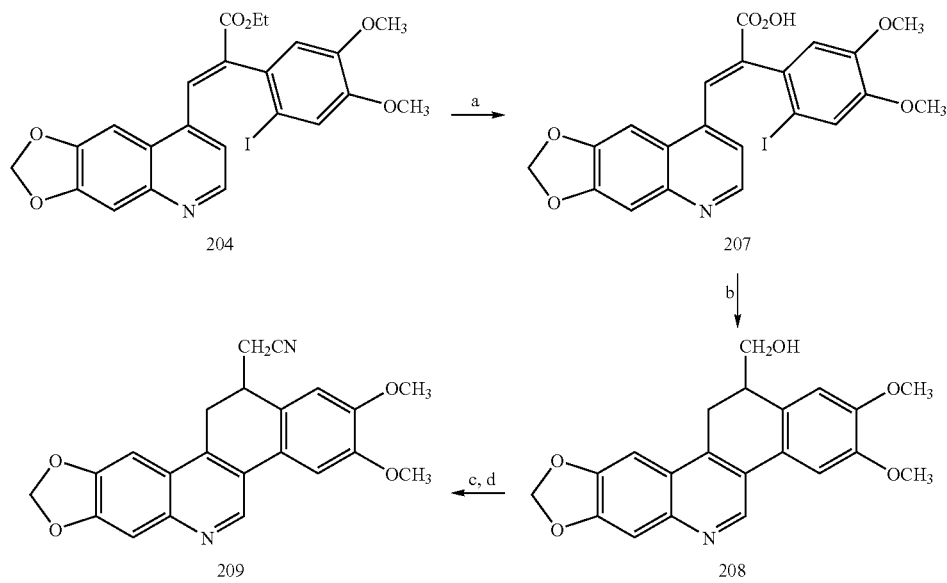

(a) NaBH₄, EtOH.
(b) hν, MeCN.
(c) MsCl, TEA, CH₂Cl₂.
(d) NaCN, EtOH

Example 3

Synthesis of Compound 208

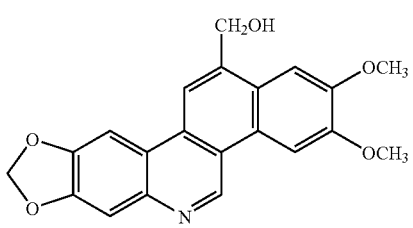

A solution of compound 207 (246 mg, 0.5 mmol) in acetonitrile (800 mg) was transferred to the photoreactor apparatus and was degassed by nitrogen purge for 30 minutes. The solution was then irradiated through a vycor filter for 90 minutes. The mixture was removed from the photoreactor, and an equal portion of 207 (246 mg, 0.5 mmol) in acetonitrile (800 mg) was reacted according to the same procedure. The solution, which had turned deep red during irradiation, was evaporated and the residue was chromatographed eluting with 98:2 chloroform-methanol, to provide 85 mg of compound 208, in 24% yield; mp 231–233° C.; $^1$H NMR (CDCl$_3$) δ 3.13 (m, 2H), 3.55 (m, 3H), 3.96 (s, 3H), 4.00 (s, 3H), 6.11 (d, 2H), 6.89 (s, 1H), 7.35 (s, 1H), 7.36 (s, 1H), 7.40 (s, 1H), 9.02 (s, 1H); $^{13}$C NMR (CDCl$_3$) δ 25.6, 40.2, 56.2, 56.4, 64.5, 99.1, 101.9, 106.5, 107.4, 112.2, 124.2, 124.7, 124.9, 129.1, 137.6, 143.7, 145.6, 148.5, 149.0, 149.2, 150.1; HRMS calcd for C$_{21}$H$_{19}$NO$_5$H: 366.1341; found: 366.1356.

The intermediate compound 207 was prepared as follows.

a. Synthesis of compound 207. Sodium borohydride (197 mg, 5.2 mmol) was added to a mixture of 104 (275 mg, 0.52 mmol) in ethanol (15 mL) at room temperature, and the mixture was heated to reflux with stirring for 1 h. The mixture was cooled and quenched by the addition of water (1 mL), and was then evaporated under vacuum. The residue was partitioned between chloroform (50 mL) and sat. NaHCO$_3$ (50 mL), and the organic phase was washed with sat. NaHCO$_3$ (2×50 mL), dried (MgSO$_4$), and evaporated, yielding 234 mg, in 92% yield; mp 90–92° C.; $^1$H NMR (CDCl$_3$) δ 1.25 (m, 1H), 1.40 (m, 1H), 3.18 (m, 1H), 3.50 (m, 1H), 3.65 (m, 1H), 3.85 (s, 3H), 3.86 (s, 3H), 6.13 (s, 2H), 6.82 (s, 1H), 6.97 (d, 1H, J=4.6), 7.21 (s, 1H), 7.40 (s, 1H), 7.42 (s, 1H), 8.51 (d, 1H, J=4.6); $^{13}$C NMR (CDCl$_3$) δ 35.0, 51.0, 56.1, 56.2, 65.3, 90.4, 99.4, 101.8, 106.4, 110.5, 120.7, 122.2, 124.8, 136.1, 144.3, 146.7, 147.5 148.2, 148.7, 149.8, 150.4; HRMS calcd for C$_{21}$H$_{20}$INO$_5$H: 494.0464; found: 494.0480.

Example 4

Synthesis of Compound 209

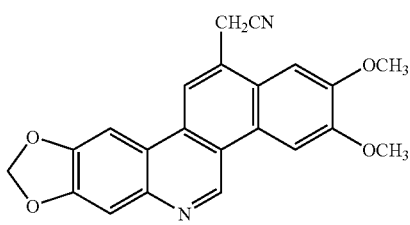

Methanesulfonyl chloride (31 μL, 0.4 mmol) was added to a cooled solution of 208 (65 mg, 0.18 mmol) and TEA (0.1 mL, 0.7 mmol) in methylene chloride (15 mL). Cooling was removed and the solution was stirred for 2 h at room temperature. The reaction mixture was then washed with sat. NaHCO$_3$ (3×30 mL), was evaporated, and the residue was chromatographed in chloroform, providing 75 mg of the mesylate, which was not characterized, but was used immediately in the next step. The mesylate was added to 15 mL of 95% ethanol, and sodium cyanide (30 mg, 0.6 mmol) was added. The mixture was heated to reflux for 7 h. The mixture was cooled and evaporated, and the residue was dissolved in chloroform (50 mL) and washed with water (3×50 mL), was evaporated, and chromatographed in 99:1 chloroform-methanol, provid 46 mg (65%). This material, which was of about 85% purity, was recrystallized from ethanol/methanol/hexanes, providing 25 mg of material of purity >95%; mp 212–214° C.; $^1$H NMR (CDCl$_3$) δ 2.41 (m, 2H), 3.22 (m, 1H), 3.45 (m, 1H), 3.53 (m, 1H), 3.99 (s, 3H), 4.02 (s, 3H), 6.15 (s, 2H), 6.90 (s, 1H), 7.36 (s, 1H), 7.42 (s, 2H), 9.08 (s, 1H); $^{13}$C NMR (CDCl$_3$) δ 22.4, 28.5, 35.1, 56.3, 56.4, 98.9, 102.0, 106.7, 107.5, 111.4, 118.3, 124.0, 124.1, 124.4, 128.6, 135.4, 143.7, 146.0, 148.9, 149.5, 149.6, 150.4; HRMS calcd for C$_{22}$H$_{18}$N$_2$O$_4$H: 375.1346; found 375.1332.

Example 5

Other representative compounds of the invention (e.g. compounds 215, 216, 218, and 219) can be prepared as illustrated in Schemes D–F.

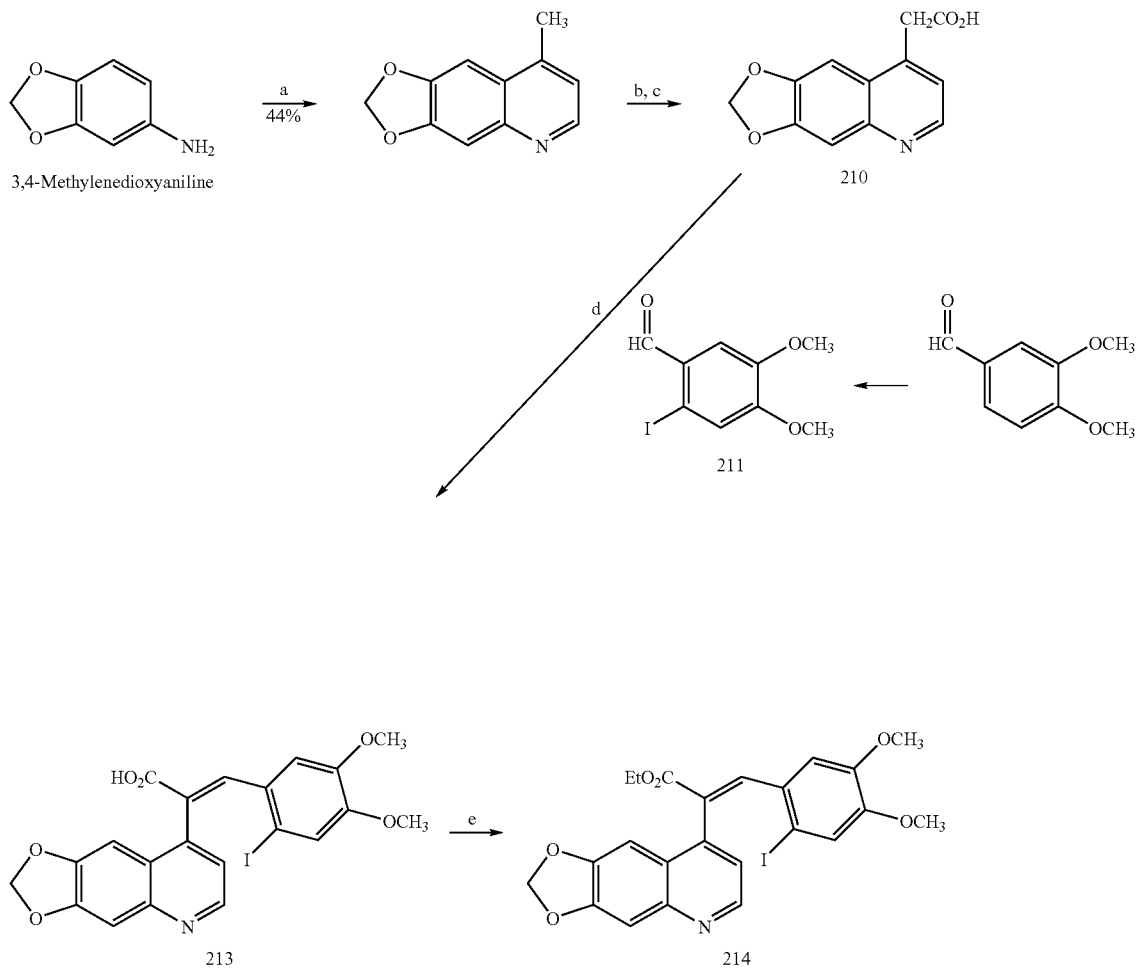

(a) methyl vinyl ketone, FeCl$_3$, AcOH.
(b) LDA, THF
(c) CO$_2$, solid.
(c) Ac$_2$O, TEA.
(d) SOCl$_2$, EtOH.

Scheme E
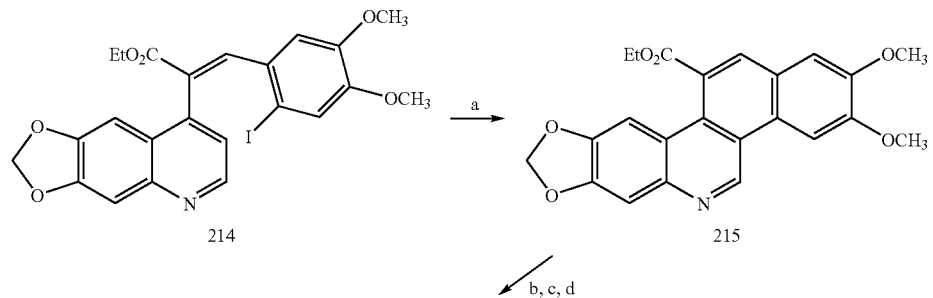
(a) hν, MeCN.
(b) NaOH, H₂O, EtOH.
(c) SOCl₂.
(d) N,N-dimethylenediamine
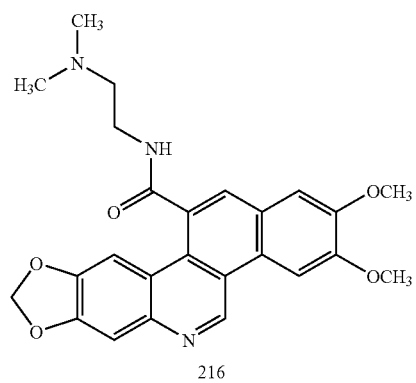
Scheme F
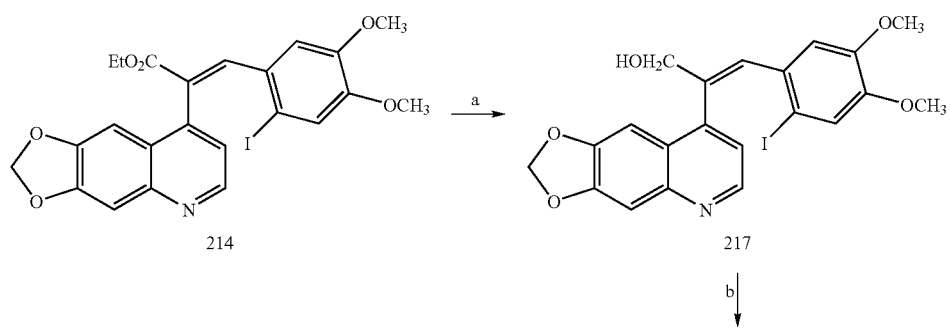
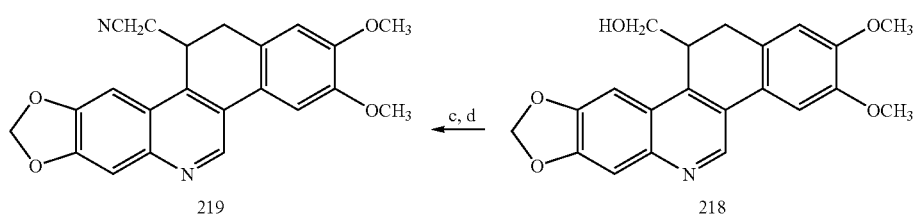
(a) NaBH₄, EtOH.
(b) hν, MeCN.
(c) MsCl, TEA, CH₂Cl₂.
(d) NaCN, EtOH

Example 6

The following illustrate representative pharmaceutical dosage forms, containing a compound of formula I or II ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (vi) Injection 3 (1 mg/ml) | mg/ml |
|---|---|
| 'Compound X' (free base form) | 1.0 |
| Citric Acid | 0.1% |
| D5W | q.s. ad 1 mL |

| (vii) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I or formula II:

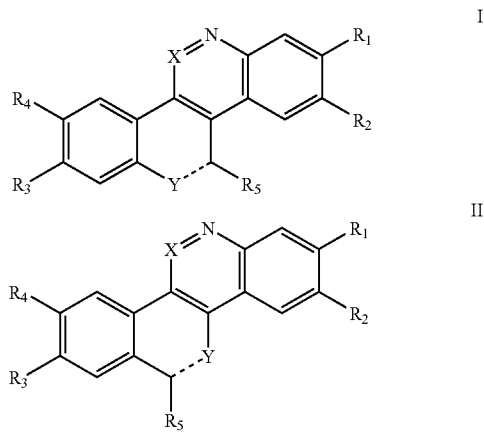

wherein:
the bond represented by --- is a single bond or a double bond;
X is CH or N;
Y is CH or N when the bond represented by --- is a double bond, or Y is $CH_2$ or $NR_x$ when the bond represented by --- is a single bond;
one of $R_1$ and $R_2$ is nitro, halo, or $(C_1–C_6)$alkoxy and the other is hydrogen, nitro, halo, or $(C_1–C_6)$alkoxy; or $R_1$ and $R_2$ taken together are methylenedioxy;
one of $R_3$ and $R_4$ is nitro, halo, or $(C_1–C_6)$alkoxy and the other of $R_3$ and $R_4$ is hydrogen, nitro, halo, or $(C_1–C_6)$alkoxy; or $R_3$ and $R_4$ taken together are methylenedioxy;
$R_5$ is a solubilizing group; and
$R_x$ is hydrogen or $(C_1–C_6)$alkyl;
or a pharmaceutically acceptable salt thereof;
provided that Y is not N, when $R_5$ is —OH.

2. The compound of claim 1 wherein X is CH.

3. A compound of formula I or formula II:

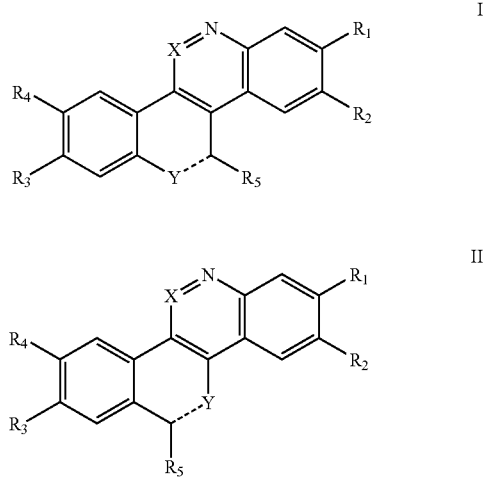

wherein:
the bond represented by --- is a double bond;
X is CH or N;
Y is CH;
one of $R_1$ and $R_2$ is nitro, halo, or $(C_1-C_6)$alkoxy and the other is hydrogen. nitro, halo, or $(C_1-C6)$alkoxy; or $R_1$ and $R_2$ taken together are methylenedioxy;
one of $R_3$ and $R_4$ is nitro, halo, or $(C_1-C_6)$alkoxy and the other is $R_3$ and $R_4$ is hydrogen, nitro, halo, or $(C_1-C_6)$alkoxy; or $R_3$ and $R_4$ taken together are methylenedioxy; and
$R_5$ is a solubilizing group;
or a pharmaceutically acceptable salt thereof.

4. The compound of claim 1 wherein $R_1$ and $R_2$ taken together are methylenedioxy.

5. The compound of claim 1 wherein $R_3$ and $R_4$ both $(C_1-C_6)$alkoxy.

6. The compound of claim 1 wherein $R_1$ and $R_2$ taken together are methylenedioxy; and $R_3$ and $R_4$ are each methoxy.

7. The compound of claim 1 wherein $R_5$ is $(C_1-C_6)$alkoxycarbonyl, cyano, halo, hydroxy, mercapto, carboxy, nitro, pyrrolidinyl, piperidinyl, imidazolidinyl, imidazolinyl, piperazinyl, morpholinyl, thiomorpholinyl, or $-NR_fR_g$, wherein $R_f$ and $R_g$ may be the same or different and are chosen from hydrogen, $(C_1-C_6)$alkyl, and $(C_3-C_6)$cycloalkyl.

8. A compound of formula I or formula II:

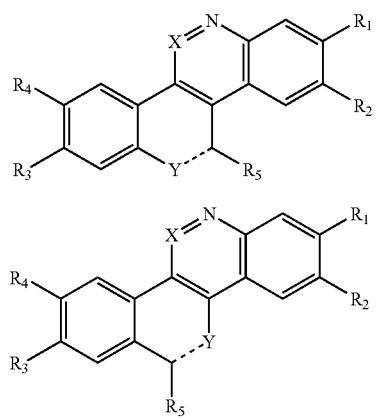

wherein:
the bond represented by --- is a single bond or a double bond;
X is CH or N;
Y is CH or N when the bond represented by --- is a double bond, or Y is $CH_2$ or $NR_x$ when the bond represented by is - - - a single bond;
one of $R_1$ and $R_2$ is nitro, halo, or $(C_1-C_6)$alkoxy and the other is hydrogen, nitro, halo, or $(C_1-C_6)$alkoxy; or $R_1$ and $R_2$ taken together are methylenedioxy;
one of $R_3$ and $R_4$ is nitro, halo, or $(C_1-C_6)$alkoxy and the other of $R_3$ and R4 is hydrogen, nitro, halo, or $(C_1-C_6)$alkoxy; or $R_3$ and $R_4$ taken together are methylenedioxy;
$R_5$ is $-W-Z$;
W is absent, $-(C=O)-$, $-CH_2-$, $-(C=O)O-$, $-O(C=O)-$, $-O-$, $-NR_a(C=O)-$, $-C(=O)NR_a-$, or $-NR_a-$;

Z is $(C_1-C_4$alkyl substituted with one or more water solubilizing groups;
$R_a$ is hydrogen or $(C_1-C_4)$alkyl; and
$R_x$ is hydrogen or $(C_1-C_6)$alkyl;
or a pharmaceutically acceptable salt thereof.

9. The compound of claim 8 wherein $-W-Z$ is $(C_1-C_4)$alkyl substituted with one or more $(C_1-C_6)$alkoxycarbonyl, cyano, halo, hydroxy, mercapto, oxo, carboxy, nitro, pyrrolidinyl, piperidinyl, imidazolidinyl, imidazolinyl, piperazinyl, morpholinyl, thiomorpholinyl, or $-NR_fR_g$ groups, wherein $R_f$ and $R_g$ may be the same or different and are chosen from hydrogen, $(C_1-C_6)$alkyl, and $(C_3-C_6)$cycloalkyl.

10. The compound of claim 8 wherein $-W-Z$ is $-CH_2CH_2-NR_fR_g$ wherein $R_f$ and $R_f$ are each independently hydrogen or $(C_1-C_6)$alkyl.

11. The compound of claim 8 wherein $-W-Z$ is $(C_2-C_4)$ alkylamino substituted with one or more $(C_1-C_6)$alkoxycarbonyl, cyano, halo, hydroxy, mercapto, oxo, carboxy, nitro, pyrrolidinyl, piperidinyl, imidazolidinyl, imidazolinyl, piperazinyl, morpholinyl, thiomorpholinyl, or $-NR_fR_g$ groups, wherein $R_f$ and $R_g$ may be the same or different and are chosen from hydrogen, $(C_1-C_6)$alkyl, and $(C_3-C_6)$cycloalkyl.

12. The compound of claim 8 wherein $-W-Z$ is $(C_1-C_4)$ alkylaminocarbonyl substituted with one $N(CH_3)_2$ group.

13. The compound of claim 1 wherein the bond represented --- is a single bond.

14. A compound of fommia I or formula II:

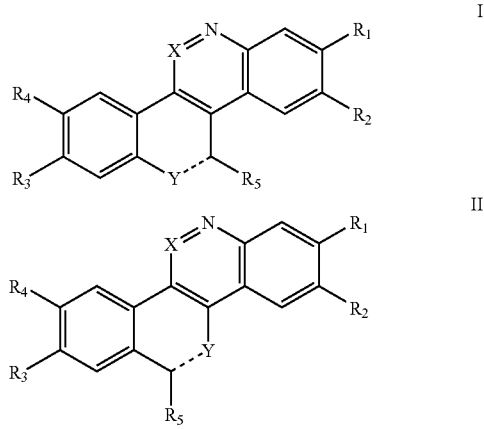

wherein:
the bond represented by --- is a double bond;
X is CH or N;
Y is CH or N;
one of $R_1$ and $R_2$ is nitro, halo, or $(C_1-C_6)$alkoxy and the other is hydroaen, nitro, halo, or $(C_1-C_6)$alkoxy; or $R_1$ and $R_2$ taken together are methylenedioxy;
one of $R_3$ and $R_4$ is nitro, halo, or $(C_1-C_6)$alkoxy and the other of $R_3$ and $R_4$ is hydrogen, nitro, halo, or $(C_1-C_6)$alkoxy; or $R_3$ and $R_4$ taken together are methylenedioxy; and
$R_5$ is a solubilizing group;
or a pharmaceutically acceptable salt thereof;
provided that Y is not N, when $R_5$ is $-OH$.

15. A pharmaceutical composition comprising a compound as described in claim 1 in combination with a pharmaceutically acceptable diluent or carrier.

16. A method of producing an antibacterial effect in a mammal in need of such treatment comprising administering to the mammal, an amount of a compound as described in claim 1, effective to provide an antibacterial effect.

17. A method of producing an antifungal effect in a mammal in need of such treatment comprising administering to the mammal, an amount of a compound as described in claim 1, effective to provide an antifungal effect.

18. A compound of formula I or formula II:

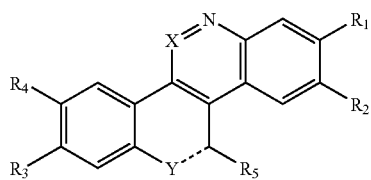

I

-continued

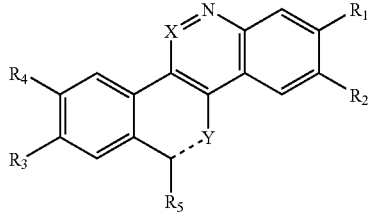

II wherein:
the bond represented by --- is a single bond or a double bond;
X is CH or N;
Y is CH or N when the bond represented by --- is a double bond, or Y is $CH_2$ or $NR_x$ when the bond represented by --- is a single bond;
one of $R_1$ and $R_2$ is nitro, halo, or $(C_1$–$C_6)$alkoxy and the other is hydrogen, nitro, halo, or $C_1$–$C_6$)alkoxy; or $R_1$ and $R_2$ taken together are methylenedioxy;
one of $R_3$ and $R_4$ is nitro, halo, or $(C_1$–$C_6)$alkoxy and the other of $R_3$ and $R_4$ is hydrogen, nitro, halo, or $(C_1$–$C_6)$ alkoxy; or $R_3$ and $R_4$ taken together are methylenedioxy;
$R_5$ is a solubilizing group; and
$R_x$ is hydrogen or $(C_1$–$C_6)$alkyl;
or a pharmaceutically acceptable salt thereof; provided that $R_5$ is not —OH.

* * * * *

UNITED STATES PATENT AND TRADEMARK OFFICE
CERTIFICATE OF CORRECTION

| | | |
|---|---|---|
| PATENT NO. | : 7,208,492 B2 | Page 1 of 1 |
| APPLICATION NO. | : 11/121292 | |
| DATED | : April 24, 2007 | |
| INVENTOR(S) | : Edmond J. LaVoie et al. | |

It is certified that error appears in the above-identified patent and that said Letters Patent is hereby corrected as shown below:

On the Title page, in the Attorney, Agent or Firm name (Field 74), delete "Viknins" and insert --Viksnins-- and delete "Pady" and insert --Padys--.

Column 51, line 6, in Claim 3, change "6" into a subscript.

Column 51, line 56, in Claim 8, delete " is - - -" and insert -- - - - is--

Column 51, line 61, in Claim 8, change "4" into a subscript.

Column 52, line 1, in Claim 8, insert --)-- after "C4".

Column 52, line 30, in Claim 13, insert --by-- after "represented".

Column 52, line 31, in Claim 14, delete "fommia" and insert --formula--.

Column 52, line 58, in Claim 14, delete "hydroaen" and insert --hydrogen--.

Column 54, line 21, in Claim, 18, insert --(-- before "C1".

Signed and Sealed this

Sixth Day of November, 2007

JON W. DUDAS
*Director of the United States Patent and Trademark Office*